US009951106B2

United States Patent
Guan et al.

(10) Patent No.: US 9,951,106 B2
(45) Date of Patent: Apr. 24, 2018

(54) RECOMBINANT FUSION PROTEIN COMPRISING HIV GP120 LINKED TO AN ENHANCING CD4 BINDING SITE MAB

(71) Applicants: Yongjun Guan, Clarksville, MD (US); George Lewis, Baltimore, MD (US); Anthony Devico, Alexandria, VA (US); Mohammad Sajadi, Cockeysville, MD (US); Tongyun Liu, Abingdon, MD (US); Marzena Pazgier, Mt. Airy, MD (US)

(72) Inventors: Yongjun Guan, Clarksville, MD (US); George Lewis, Baltimore, MD (US); Anthony Devico, Alexandria, VA (US); Mohammad Sajadi, Cockeysville, MD (US); Tongyun Liu, Abingdon, MD (US); Marzena Pazgier, Mt. Airy, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/649,565

(22) PCT Filed: Dec. 4, 2013

(86) PCT No.: PCT/US2013/073003
§ 371 (c)(1),
(2) Date: Jun. 4, 2015

(87) PCT Pub. No.: WO2014/089152
PCT Pub. Date: Jun. 12, 2014

(65) Prior Publication Data
US 2015/0299268 A1    Oct. 22, 2015

Related U.S. Application Data

(60) Provisional application No. 61/733,172, filed on Dec. 4, 2012, provisional application No. 61/886,370, filed on Oct. 3, 2013.

(51) Int. Cl.
| | |
|---|---|
| C07K 14/005 | (2006.01) |
| C07K 14/16 | (2006.01) |
| C07K 16/10 | (2006.01) |
| A61K 39/12 | (2006.01) |
| A61K 39/21 | (2006.01) |
| A61K 39/00 | (2006.01) |

(52) U.S. Cl.
CPC ............ *C07K 14/005* (2013.01); *A61K 39/12* (2013.01); *C07K 14/162* (2013.01); *C07K 16/1063* (2013.01); *A61K 39/21* (2013.01); *A61K 2039/505* (2013.01); *C07K 2317/31* (2013.01); *C07K 2317/34* (2013.01); *C07K 2317/56* (2013.01); *C07K 2317/622* (2013.01); *C07K 2317/76* (2013.01); *C07K 2318/10* (2013.01); *C07K 2319/00* (2013.01); *C07K 2319/40* (2013.01); *C12N 2740/16134* (2013.01)

(58) Field of Classification Search
CPC .............. C07K 14/162; C07K 16/1063; C07K 2318/10; C07K 2317/622; C07K 2319/00; A61K 39/21
See application file for complete search history.

(56) References Cited

U.S. PATENT DOCUMENTS

| 6,924,360 B2 | 8/2005 | Green et al. |
| 8,026,344 B2 | 9/2011 | Zhou et al. |

FOREIGN PATENT DOCUMENTS

| WO | 98/01564 | 1/1998 |
| WO | 2011-038290 | 3/2011 |
| WO | 2011/092593 | 8/2011 |
| WO | 2012/040562 | 3/2012 |
| WO | 2012-065055 | 5/2012 |

OTHER PUBLICATIONS

Lee, S.-K., et al., 2000, A single point mutation in HIV-1 V3 loop alters the immunogenic properties of rgp120, Arch. Virol. 145:2087-2103.*
Chen, C., et al., 1995, Enhancement and destruction fo antibody function by somatic mutation: unequal occurrence is controlled by V gene combinatorial associations, The EMBO J, 14(12):2784-2794.*
Barouch, D. H., 2008, Challenges in the development of an HIV-1 vaccine, Nature 455:613-619.*
Walker, B. D., and D. R. Burton, 2008, Toward an AIDS vaccine, Science 320:760-764.*
Extended European Search Report dated Jun. 9, 2016 in corresponding European Application No. 13861143.9.
Klein, F. et al. Broad neutralization by a combination of antibodies recognizing the CD4 binding site and a new conformational epitope on the HIV-1 envelope protein. *Science* 333(6049):1469-1479 (2012).
Genbank Accession No. ABA26068.1, dated Dec. 31, 2005.
International Search Report and Written Opinion for PCT/US13/73003, dated Mar. 26, 2014.
English Translation of Office Action dated Dec. 5, 2017 in Chinese Application No. 201380072256.7.

* cited by examiner

*Primary Examiner* — Jeffrey Parkin
(74) *Attorney, Agent, or Firm* — Wenderoth, Lind & Ponack, L.L.P.

(57) ABSTRACT

Fusion proteins comprising a portion of the HIV-1 Env protein (gp120 and gp140) and single-chain fragment V regions (ScFv) of an enhancing antibody that exhibits binding specificity for HIV-1 Env protein are disclosed that may serve in immunogenic formulations for vaccination against HIV-1 infection, as well as methods of generating an immune response using the fusion proteins.

3 Claims, 7 Drawing Sheets

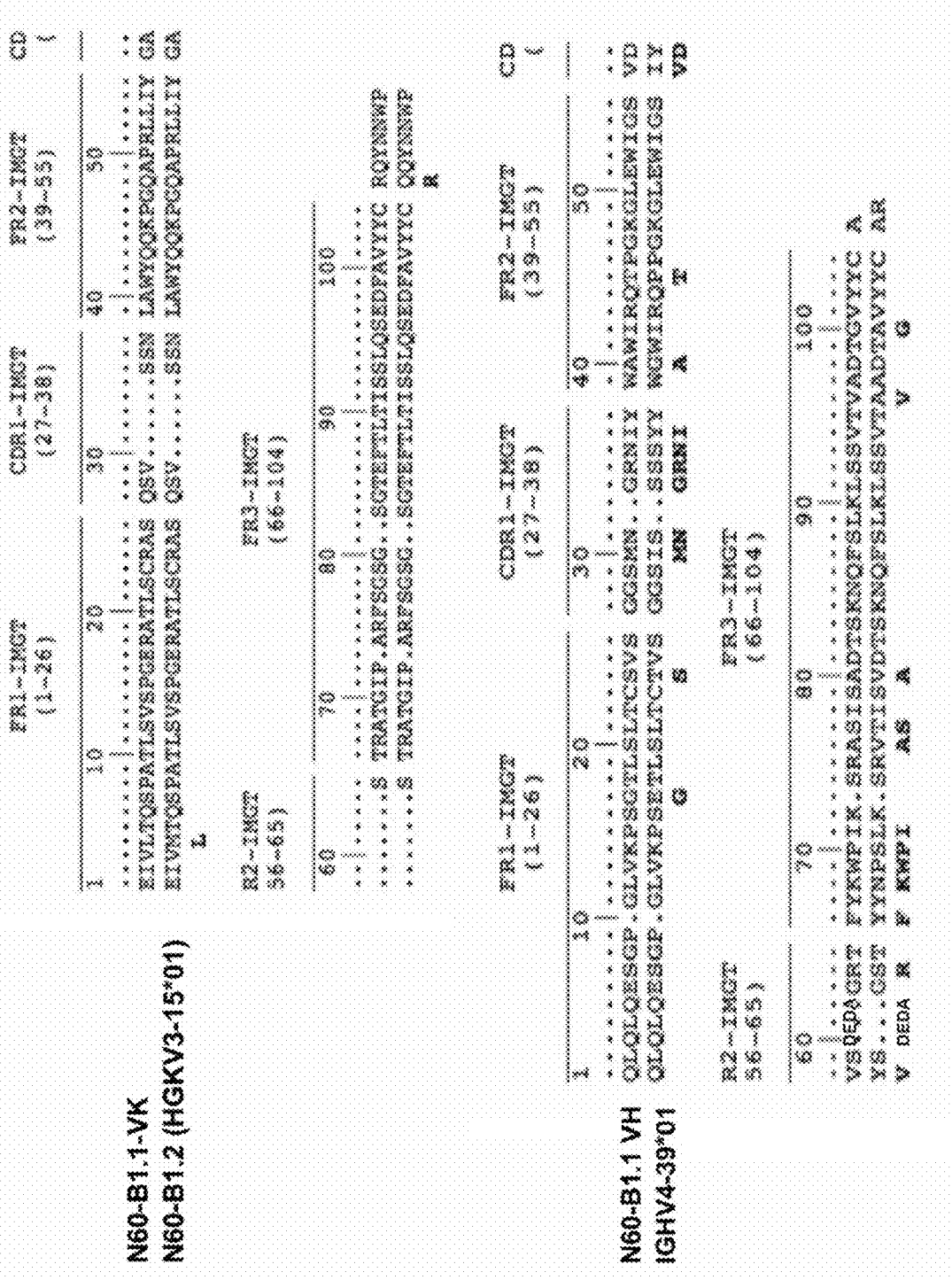
Figure 1. Sequences of Heavy and Light Chains of N60-B1.1

Figure 2. N60-B1.1 against an epitope of co-receptor-associated-region involving V1/V2 and V3

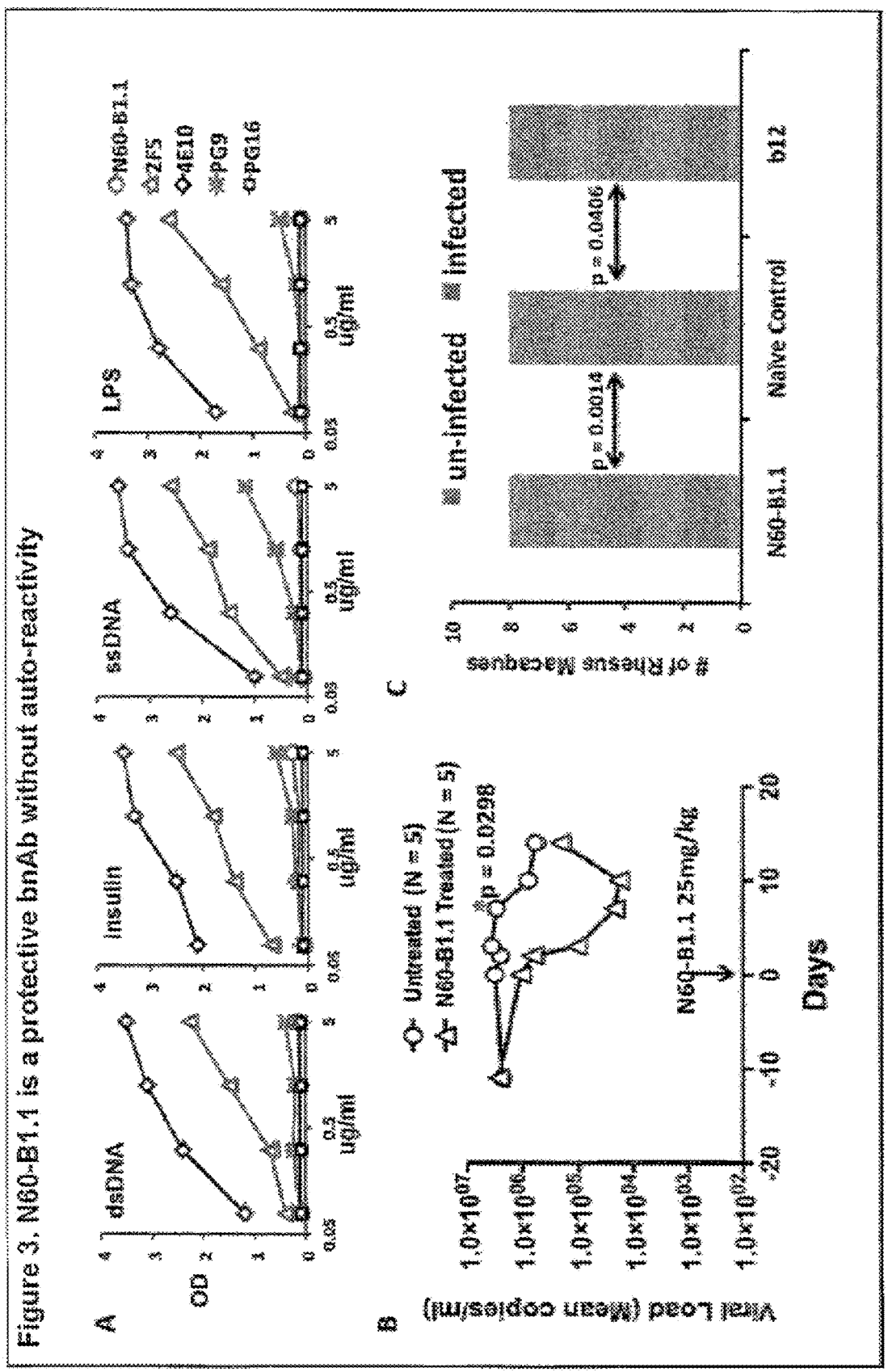

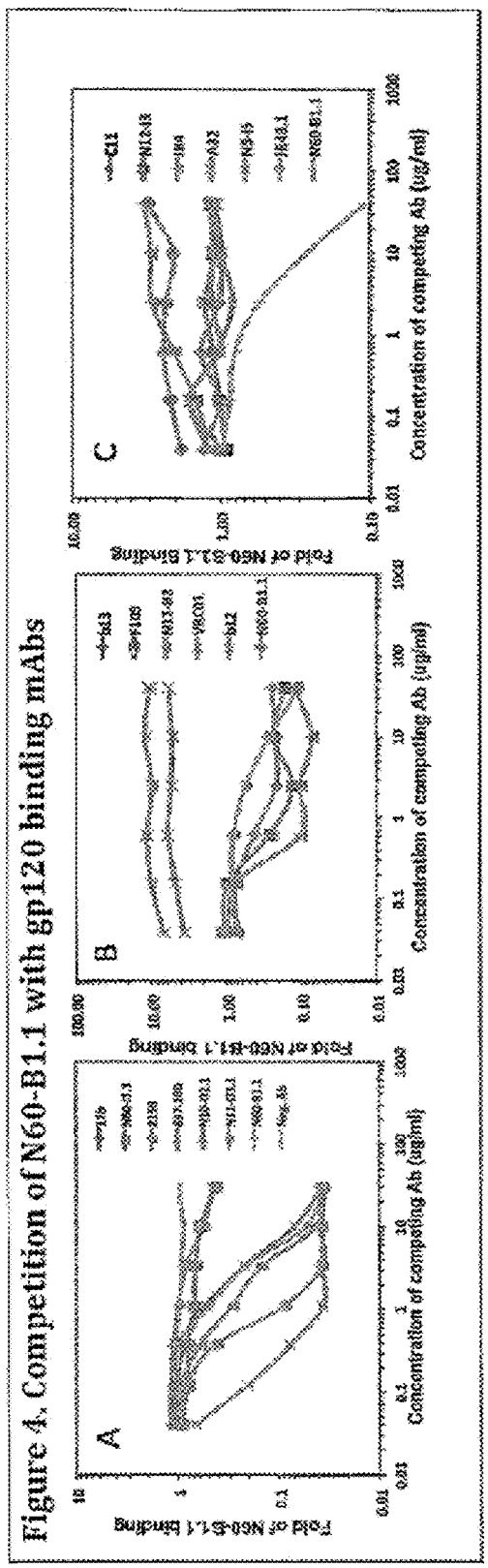

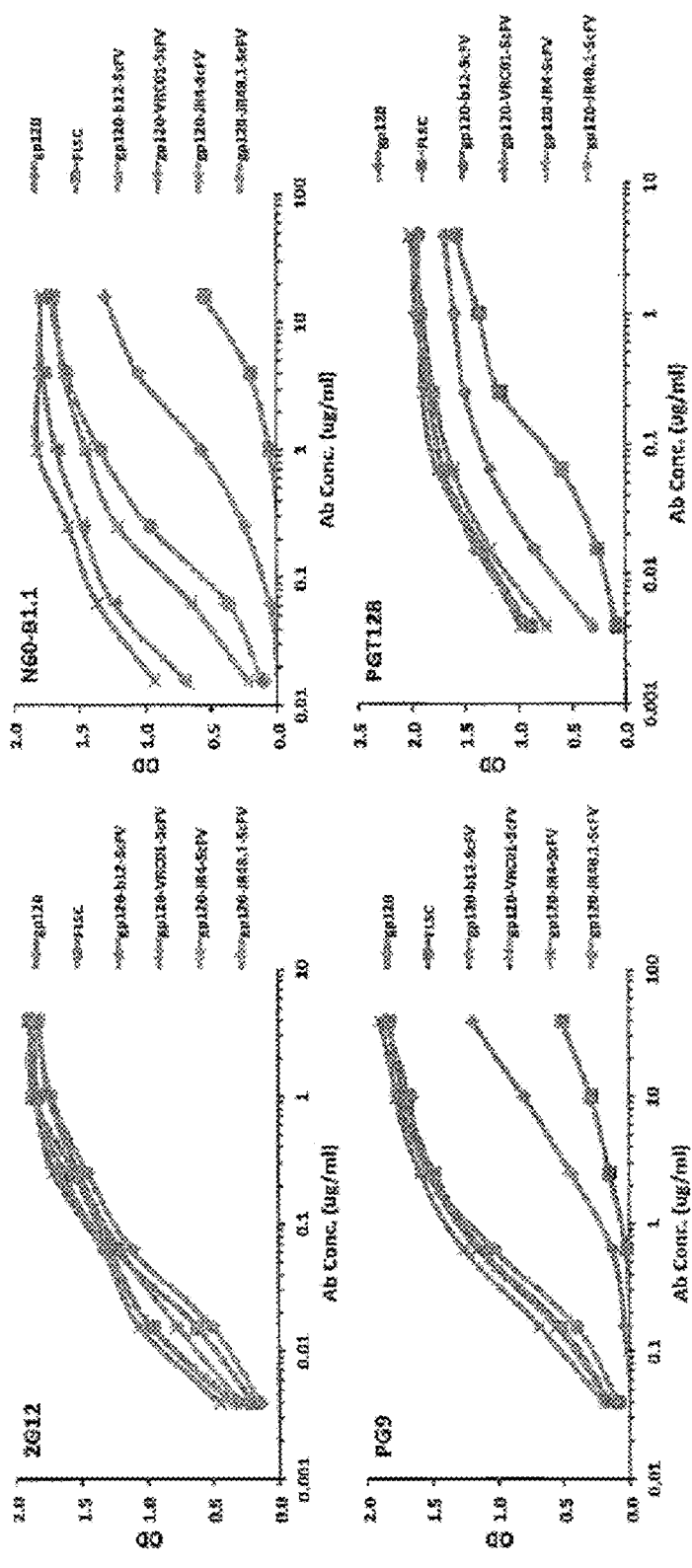

Figure 6. Enhanced exposure of ADCC Abs' epitopes in gp120-b12/VRC01 ScFv fusion proteins

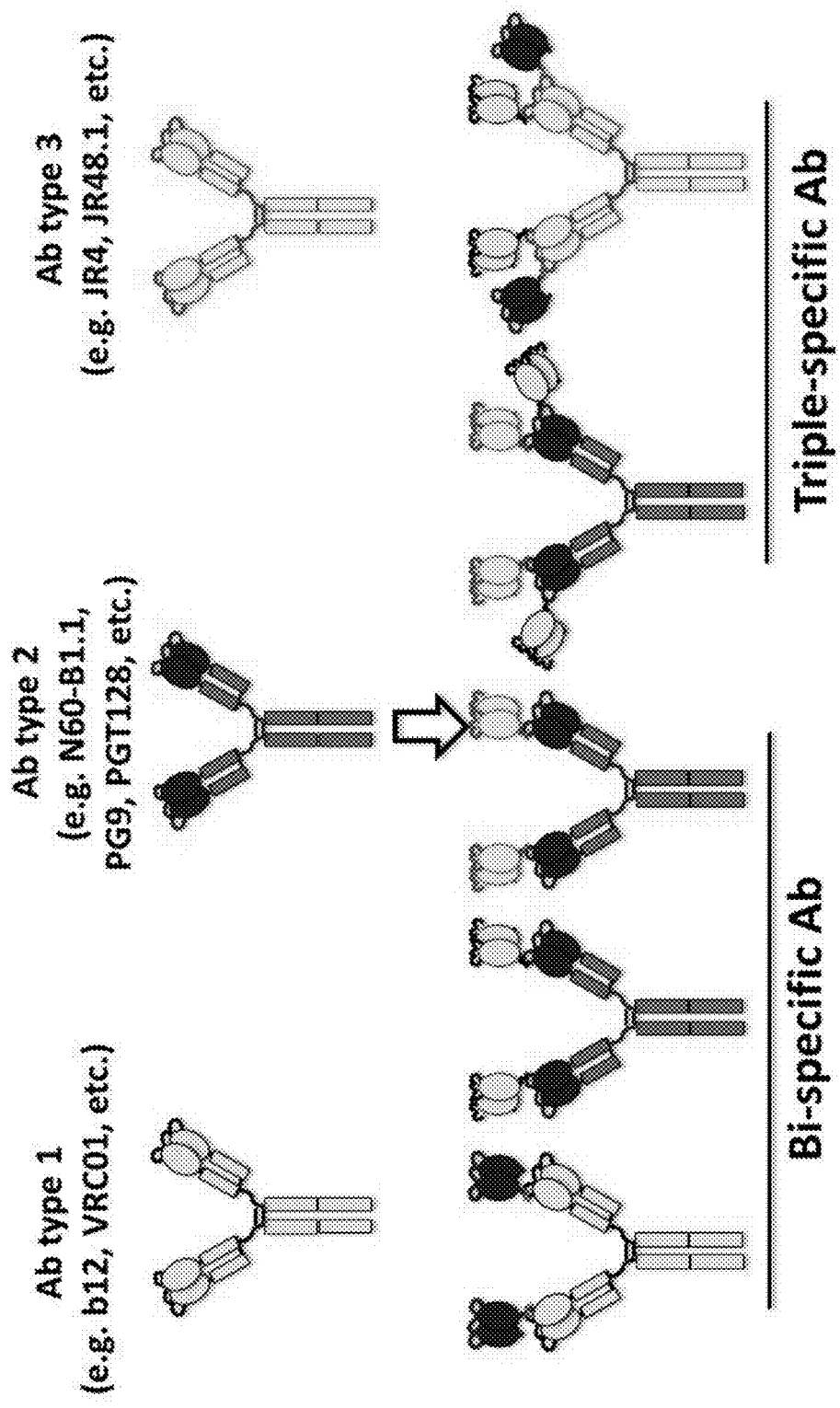

SEQUENCE LISTING

```
<160> NUMBER OF SEQ ID NOS: 17

<210> SEQ ID NO 1
<211> LENGTH: 322
<212> TYPE: DNA
<213> ORGANISM: Homo sapien

<400> SEQUENCE: 1
gaaattgtgt tgacacagtc tccagccacc ctgtctgtgt ctccagggga aagagccacc        60
ctctcctgca gggccagtca gagtgttagc agcaacttag cctggtacca gcagaaacct       120
ggccaggctc ccaggctcct catctatggt gcatccacca gggccactgg tatcccagcc       180
aggttcagtg gcagtgggtc tgggacagag ttcactctca ccatcagcag cctgcagtct       240
gaagattttg cagtttatta ctgtcggcag tataataact ggcctcagac gttcggccaa       300
gggaccaaag tggatatcaa ac                                                322

<210> SEQ ID NO 2
<211> LENGTH: 107
<212> TYPE: PRT
<213> ORGANISM: Homo sapien

<400> SEQUENCE: 2

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Arg Gln Tyr Asn Asn Trp Pro Gln
                85                  90                  95

Thr Phe Gly Gln Gly Thr Lys Val Asp Ile Lys
            100                 105

<210> SEQ ID NO 3
<211> LENGTH: 434
<212> TYPE: DNA
<213> ORGANISM: Homo sapien

<400> SEQUENCE: 3
cagctgcagc tgcaggagtc gggcccagga ctggtgaagc cttcggggac cctgtccctc        60
acctgctctg tctctggtgg ctccatgaac ggtcgaaata tctattgggc ctggatccgc       120 cagacccag ggaaggggct ggagtggatt ggaagtgttg atgtaagtga tgaggatgcc        180
gggcgcacgt tttataagtg gcccattaag agtcgagcct ccatatccgc agacacgtcc       240
```

```
aagaatcagt tctccctgaa actgagctct gtgaccgtcg cagacacggg tgtctattac      300
tgtgcgcggg agactttata ctatgttggc aatggttatt actaccctct ggatgttttc      360
tactacaact attacatgga cgtctggggc aaggggacca cggtcagtgt ctcctcagcc      420
tccaccaagg gccc                                                         434
```

<210> SEQ ID NO 4
<211> LENGTH: 144
<212> TYPE: PRT
<213> ORGANISM: Homo sapien

<400> SEQUENCE: 4

```
Gln Leu Gln Leu Gln Glu Ser Gly Pro Gly Leu Val Lys Pro Ser Gly
1               5                   10                  15

Thr Leu Ser Leu Thr Cys Ser Val Ser Gly Gly Ser Met Asn Gly Arg
            20                  25                  30

Asn Ile Tyr Trp Ala Trp Ile Arg Gln Thr Pro Gly Lys Gly Leu Glu
        35                  40                  45

Trp Ile Gly Ser Val Asp Val Ser Asp Glu Asp Ala Gly Arg Thr Phe
50                  55                  60

Tyr Lys Trp Pro Ile Lys Ser Arg Ala Ser Ile Ser Ala Asp Thr Ser
65                  70                  75                  80

Lys Asn Gln Phe Ser Leu Lys Leu Ser Ser Val Thr Val Ala Asp Thr
                85                  90                  95

Gly Val Tyr Tyr Cys Ala Arg Glu Thr Leu Tyr Tyr Val Gly Asn Gly
            100                 105                 110

Tyr Tyr Tyr Pro Leu Asp Val Phe Tyr Tyr Asn Tyr Tyr Met Asp Val
        115                 120                 125

Trp Gly Lys Gly Thr Thr Val Ser Val Ser Ser Ala Ser Thr Lys Gly
    130                 135                 140
```

<210> SEQ ID NO 5
<211> LENGTH: 95
<212> TYPE: PRT
<213> ORGANISM: Homo sapien

<400> SEQUENCE: 5

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 6
<211> LENGTH: 99
<212> TYPE: PRT
<213> ORGANISM: Homo sapien

<400> SEQUENCE: 6

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Ile Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg
```

<210> SEQ ID NO 7
<211> LENGTH: 2349
<212> TYPE: DNA
<213> ORGANISM: Artificial Sequence
<220> FEATURE:
<223> OTHER INFORMATION: chemically-synthesized gp120-ScFV construct
      comprising gp120-b12-ScFV
<220> FEATURE:
<221> NAME/KEY: CDS
<222> LOCATION: (1)..(2349)

<400> SEQUENCE: 7

```
atg aga gtg acc gag atc aga aag tcc tac cag cat tgg tgg aga tgg      48
Met Arg Val Thr Glu Ile Arg Lys Ser Tyr Gln His Trp Trp Arg Trp
1               5                   10                  15 gga atc atg ctg ctc gga atc ctg atg atc tgc aac gcc gag gag aag      96
Gly Ile Met Leu Leu Gly Ile Leu Met Ile Cys Asn Ala Glu Glu Lys
            20                  25                  30 ctg tgg gtg acc gtg tac tac ggc gtg ccc gtg tgg aag gag gcc acc     144
Leu Trp Val Thr Val Tyr Tyr Gly Val Pro Val Trp Lys Glu Ala Thr
        35                  40                  45 acc acc ctg ttc tgc gcc agc gac cgc aag gcc tac gac acc gag gtg     192
Thr Thr Leu Phe Cys Ala Ser Asp Arg Lys Ala Tyr Asp Thr Glu Val
    50                  55                  60 cac aac gtg tgg gcc acc cac gcc tgc gtg ccc acc gac ccc aac ccc     240
His Asn Val Trp Ala Thr His Ala Cys Val Pro Thr Asp Pro Asn Pro
65                  70                  75                  80 cag gag gtg gag ctg aag aac gtg acc gag aac ttc aac atg tgg aag     288
Gln Glu Val Glu Leu Lys Asn Val Thr Glu Asn Phe Asn Met Trp Lys
            85                  90                  95 aac aac atg gtg gag cag atg cac gag gac atc atc agc ctg tgg gac     336
Asn Asn Met Val Glu Gln Met His Glu Asp Ile Ile Ser Leu Trp Asp
            100                 105                 110 cag agc ctg aag ccc tgc gtg aag ctg acc ccc ctg tgc gtg acc ctg     384
Gln Ser Leu Lys Pro Cys Val Lys Leu Thr Pro Leu Cys Val Thr Leu
        115                 120                 125 aac tgc acc gac ctg cgc aac gcc acc aac ggc aac gac acc aac acc     432
Asn Cys Thr Asp Leu Arg Asn Ala Thr Asn Gly Asn Asp Thr Asn Thr
    130                 135                 140 act agt agc agc cgc ggc atg gtg ggc ggc gag atg aag aac tgc         480
Thr Ser Ser Ser Arg Gly Met Val Gly Gly Glu Met Lys Asn Cys
145                 150                 155                 160 agc ttc aac atc acc acc aac atc cgc ggc aag gtg cag aag gag tac     528
Ser Phe Asn Ile Thr Thr Asn Ile Arg Gly Lys Val Gln Lys Glu Tyr
                165                 170                 175
```

-continued

| | |
|---|---|
| gcc ctg ttc tac aag ctg gac atc gcc ccc atc gac aac aac agc aac<br>Ala Leu Phe Tyr Lys Leu Asp Ile Ala Pro Ile Asp Asn Asn Ser Asn<br>                180                        185                    190 | 576 |
| aac cgc tac cgc ctg atc agc tgc aac acc agc gtg atc acc cag gcc<br>Asn Arg Tyr Arg Leu Ile Ser Cys Asn Thr Ser Val Ile Thr Gln Ala<br>         195                        200                      205 | 624 |
| tgc ccc aag gtg agc ttc gag ccc atc ccc atc cac tac tgc gcc ccc<br>Cys Pro Lys Val Ser Phe Glu Pro Ile Pro Ile His Tyr Cys Ala Pro<br> 210                         215                      220 | 672 |
| gcc ggc ttc gcc atc ctg aag tgc aag gac aag aag ttc aac ggc aag<br>Ala Gly Phe Ala Ile Leu Lys Cys Lys Asp Lys Lys Phe Asn Gly Lys<br>225                         230                      235                      240 | 720 |
| ggc ccc tgc acc aac gtg agc acc gtg cag tgc acc cac ggc atc cgc<br>Gly Pro Cys Thr Asn Val Ser Thr Val Gln Cys Thr His Gly Ile Arg<br>                245                        250                      255 | 768 |
| ccc gtg gtg agc acc cag ctg ctg ctg aac ggc agc ctg gcc gag gag<br>Pro Val Val Ser Thr Gln Leu Leu Leu Asn Gly Ser Leu Ala Glu Glu<br>         260                        265                      270 | 816 |
| gag gtg gtg atc cgc agc gcc aac ttc gcc gac aac gcc aag gtg atc<br>Glu Val Val Ile Arg Ser Ala Asn Phe Ala Asp Asn Ala Lys Val Ile<br>        275                        280                      285 | 864 |
| atc gtg cag ctg aac gag agc gtg gag atc aac tgc acc cgc ccc aac<br>Ile Val Gln Leu Asn Glu Ser Val Glu Ile Asn Cys Thr Arg Pro Asn<br>290                         295                      300 | 912 |
| aac aac acc cgc aag tcc atc cac atc ggc ccc ggc cgc gcc ttc tac<br>Asn Asn Thr Arg Lys Ser Ile His Ile Gly Pro Gly Arg Ala Phe Tyr<br>305                         310                      315                      320 | 960 |
| acc acc ggc gag atc atc ggc gac atc cgc cag gcc cac tgc aac ctg<br>Thr Thr Gly Glu Ile Ile Gly Asp Ile Arg Gln Ala His Cys Asn Leu<br>                325                        330                      335 | 1008 |
| agc cgc gcc aag tgg aac gac acc ctg aac aag atc gtg atc aag ctg<br>Ser Arg Ala Lys Trp Asn Asp Thr Leu Asn Lys Ile Val Ile Lys Leu<br>                    340                      345                      350 | 1056 |
| cgc gag cag ttc ggc aac aag acc atc gtg ttc aag cac agc agc ggc<br>Arg Glu Gln Phe Gly Asn Lys Thr Ile Val Phe Lys His Ser Ser Gly<br>                  355                        360                      365 | 1104 |
| ggc gac ccc gag atc gtg acc cac agc ttc aat tgc ggc ggc gag ttc<br>Gly Asp Pro Glu Ile Val Thr His Ser Phe Asn Cys Gly Gly Glu Phe<br>370                         375                      380 | 1152 |
| ttc tac tgc aac agc acc cag ctg ttc aac agc acc tgg aac gtg acc<br>Phe Tyr Cys Asn Ser Thr Gln Leu Phe Asn Ser Thr Trp Asn Val Thr<br>385                         390                      395                      400 | 1200 |
| gag gag agc aac aac acc gtg gag aac aac acc atc acc ctg ccc tgc<br>Glu Glu Ser Asn Asn Thr Val Glu Asn Asn Thr Ile Thr Leu Pro Cys<br>                    405                      410                      415 | 1248 |
| cgc atc aag cag atc atc aac atg tgg cag gag gtg ggc cgc gcc atg<br>Arg Ile Lys Gln Ile Ile Asn Met Trp Gln Glu Val Gly Arg Ala Met<br>                    420                      425                      430 | 1296 |
| tac gcc ccc ccc atc cgc ggc cag atc cgc tgc agt tcg aac atc acc<br>Tyr Ala Pro Pro Ile Arg Gly Gln Ile Arg Cys Ser Ser Asn Ile Thr<br>                435                        440                      445 | 1344 |
| ggc ctg ctg ctg acc cgc gac ggc ggc ccc gag gac aac aag acc gag<br>Gly Leu Leu Leu Thr Arg Asp Gly Gly Pro Glu Asp Asn Lys Thr Glu<br>450                         455                      460 | 1392 |
| gtg ttc cgc ccc ggc ggc ggc gac atg cgc gac aac tgg cgc agc gag<br>Val Phe Arg Pro Gly Gly Gly Asp Met Arg Asp Asn Trp Arg Ser Glu<br>465                         470                      475                      480 | 1440 |
| ctg tac aag tac aag gtg gtg aag atc gag ccc ctg ggc gtg gcc ccc<br>Leu Tyr Lys Tyr Lys Val Val Lys Ile Glu Pro Leu Gly Val Ala Pro<br>                    485                      490                      495 | 1488 |

```
acc aag gcc aag cgc cgc gtg gtg cag cgc gag aag acc gga tcc tct    1536
Thr Lys Ala Lys Arg Arg Val Val Gln Arg Glu Lys Thr Gly Ser Ser
            500                 505                 510 ggt ggc ggt ggc tcg ggc tcc gga gga ggt ggg tcg ggt ggc ggc gcg    1584
Gly Gly Gly Gly Ser Gly Ser Gly Gly Gly Gly Ser Gly Gly Gly Ala
        515                 520                 525 gcc gct cag gtc cag ctt gtg cag tct ggg gct gag gtg aag aag cct    1632
Ala Ala Gln Val Gln Leu Val Gln Ser Gly Ala Glu Val Lys Lys Pro
    530                 535                 540 ggg gcc tca gtg aag gtt tcc tgc cag gct tct gga tac agg ttc agc    1680
Gly Ala Ser Val Lys Val Ser Cys Gln Ala Ser Gly Tyr Arg Phe Ser
545                 550                 555                 560 aac ttc gtg atc cat tgg gtg cgc cag gcc ccc gga caa agg ttc gag    1728
Asn Phe Val Ile His Trp Val Arg Gln Ala Pro Gly Gln Arg Phe Glu
                565                 570                 575 tgg atg gga tgg atc aac cct tac aat ggt aac aag gag ttc tca gct    1776
Trp Met Gly Trp Ile Asn Pro Tyr Asn Gly Asn Lys Glu Phe Ser Ala
            580                 585                 590 aag ttc cag gac aga gtc acc ttc acc gct gac aca tcc gcg aac aca    1824
Lys Phe Gln Asp Arg Val Thr Phe Thr Ala Asp Thr Ser Ala Asn Thr
        595                 600                 605 gcc tac atg gag ctg agg agc ctg aga tct gct gac acg gct gtg tat    1872
Ala Tyr Met Glu Leu Arg Ser Leu Arg Ser Ala Asp Thr Ala Val Tyr
    610                 615                 620 tac tgt gcg aga gtg gga ccc tac agc tgg gac gac agc ccc cag gac    1920
Tyr Cys Ala Arg Val Gly Pro Tyr Ser Trp Asp Asp Ser Pro Gln Asp
625                 630                 635                 640 aac tac tac atg gac gtc tgg ggc aaa ggg acc acg gtc atc gtc tcc    1968
Asn Tyr Tyr Met Asp Val Trp Gly Lys Gly Thr Thr Val Ile Val Ser
                645                 650                 655 tca gcg tcg acc ggc ggt ggc tct ggt ggc ggc ggt tcc ggt ggc ggt    2016
Ser Ala Ser Thr Gly Gly Gly Ser Gly Gly Gly Gly Ser Gly Gly Gly
            660                 665                 670 gga tcc gaa att gtg ttg acg cag tct cca ggc acc ctg tct ttg tct    2064
Gly Ser Glu Ile Val Leu Thr Gln Ser Pro Gly Thr Leu Ser Leu Ser
        675                 680                 685 cca ggg gaa aga gcc acc ttc tcc tgc agg tcc agt cac agt att aga    2112
Pro Gly Glu Arg Ala Thr Phe Ser Cys Arg Ser Ser His Ser Ile Arg
    690                 695                 700 agc aga agg gtg gcc tgg tac cag cac aaa cct ggc cag gct ccc agg    2160
Ser Arg Arg Val Ala Trp Tyr Gln His Lys Pro Gly Gln Ala Pro Arg
705                 710                 715                 720 ctc gtg atc cac ggt gtg tcc aac agg gcc agc ggc atc agc gac agg    2208
Leu Val Ile His Gly Val Ser Asn Arg Ala Ser Gly Ile Ser Asp Arg
                725                 730                 735 ttc agt ggc agt ggg tct ggg aca gac ttc act ctc acc atc acc aga    2256
Phe Ser Gly Ser Gly Ser Gly Thr Asp Phe Thr Leu Thr Ile Thr Arg
            740                 745                 750 gtg gag cct gaa gat ttt gca ctg tat tac tgt cag gtg tat ggt gcc    2304
Val Glu Pro Glu Asp Phe Ala Leu Tyr Tyr Cys Gln Val Tyr Gly Ala
        755                 760                 765 tca agc tac act ttt ggc cag ggg acc aag ctg gag agg aaa tga        2349
Ser Ser Tyr Thr Phe Gly Gln Gly Thr Lys Leu Glu Arg Lys
770                 775                 780
```

<210> SEQ ID NO 8
<211> LENGTH: 782
<212> TYPE: PRT
<213> ORGANISM: Artificial Sequence
<220> FEATURE:
<223> OTHER INFORMATION: Synthetic Construct

```
<400> SEQUENCE: 8

Met Arg Val Thr Glu Ile Arg Lys Ser Tyr Gln His Trp Trp Arg Trp
1               5                   10                  15

Gly Ile Met Leu Leu Gly Ile Leu Met Ile Cys Asn Ala Glu Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Arg Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Glu Leu Lys Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Leu Arg Asn Ala Thr Asn Gly Asn Asp Thr Asn Thr
130                 135                 140

Thr Ser Ser Arg Gly Met Val Gly Gly Glu Met Lys Asn Cys
145                 150                 155                 160

Ser Phe Asn Ile Thr Thr Asn Ile Arg Gly Lys Val Gln Lys Glu Tyr
                165                 170                 175

Ala Leu Phe Tyr Lys Leu Asp Ile Ala Pro Ile Asp Asn Asn Ser Asn
            180                 185                 190

Asn Arg Tyr Arg Leu Ile Ser Cys Asn Thr Ser Val Ile Thr Gln Ala
        195                 200                 205

Cys Pro Lys Val Ser Phe Glu Pro Ile Pro Ile His Tyr Cys Ala Pro
210                 215                 220

Ala Gly Phe Ala Ile Leu Lys Cys Lys Asp Lys Lys Phe Asn Gly Lys
225                 230                 235                 240

Gly Pro Cys Thr Asn Val Ser Thr Val Gln Cys Thr His Gly Ile Arg
                245                 250                 255

Pro Val Val Ser Thr Gln Leu Leu Leu Asn Gly Ser Leu Ala Glu Glu
            260                 265                 270

Glu Val Val Ile Arg Ser Ala Asn Phe Ala Asp Asn Ala Lys Val Ile
        275                 280                 285

Ile Val Gln Leu Asn Glu Ser Val Glu Ile Asn Cys Thr Arg Pro Asn
290                 295                 300

Asn Asn Thr Arg Lys Ser Ile His Ile Gly Pro Gly Arg Ala Phe Tyr
305                 310                 315                 320

Thr Thr Gly Glu Ile Ile Gly Asp Ile Arg Gln Ala His Cys Asn Leu
                325                 330                 335

Ser Arg Ala Lys Trp Asn Asp Thr Leu Asn Lys Ile Val Ile Lys Leu
            340                 345                 350

Arg Glu Gln Phe Gly Asn Lys Thr Ile Val Phe Lys His Ser Ser Gly
        355                 360                 365

Gly Asp Pro Glu Ile Val Thr His Ser Phe Asn Cys Gly Gly Glu Phe
370                 375                 380

Phe Tyr Cys Asn Ser Thr Gln Leu Phe Asn Ser Thr Trp Asn Val Thr
385                 390                 395                 400

Glu Glu Ser Asn Asn Thr Val Glu Asn Asn Thr Ile Thr Leu Pro Cys
                405                 410                 415
```

Arg Ile Lys Gln Ile Ile Asn Met Trp Gln Glu Val Gly Arg Ala Met
            420                 425                 430

Tyr Ala Pro Pro Ile Arg Gly Gln Ile Arg Cys Ser Ser Asn Ile Thr
        435                 440                 445

Gly Leu Leu Leu Thr Arg Asp Gly Gly Pro Glu Asp Asn Lys Thr Glu
    450                 455                 460

Val Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Thr Gly Ser Ser
            500                 505                 510

Gly Gly Gly Gly Ser Gly Ser Gly Gly Gly Ser Gly Gly Gly Ala
            515                 520                 525

Ala Ala Gln Val Gln Leu Val Gln Ser Gly Ala Glu Val Lys Lys Pro
            530                 535                 540

Gly Ala Ser Val Lys Val Ser Cys Gln Ala Ser Gly Tyr Arg Phe Ser
545                 550                 555                 560

Asn Phe Val Ile His Trp Val Arg Gln Ala Pro Gly Gln Arg Phe Glu
                565                 570                 575

Trp Met Gly Trp Ile Asn Pro Tyr Asn Gly Asn Lys Glu Phe Ser Ala
            580                 585                 590

Lys Phe Gln Asp Arg Val Thr Phe Thr Ala Asp Thr Ser Ala Asn Thr
            595                 600                 605

Ala Tyr Met Glu Leu Arg Ser Leu Arg Ser Ala Asp Thr Ala Val Tyr
            610                 615                 620

Tyr Cys Ala Arg Val Gly Pro Tyr Ser Trp Asp Ser Pro Gln Asp
625                 630                 635                 640

Asn Tyr Tyr Met Asp Val Trp Gly Lys Gly Thr Thr Val Ile Val Ser
                645                 650                 655

Ser Ala Ser Thr Gly Gly Gly Ser Gly Gly Gly Ser Gly Gly Gly
            660                 665                 670

Gly Ser Glu Ile Val Leu Thr Gln Ser Pro Gly Thr Leu Ser Leu Ser
            675                 680                 685

Pro Gly Glu Arg Ala Thr Phe Ser Cys Arg Ser Ser His Ser Ile Arg
    690                 695                 700

Ser Arg Arg Val Ala Trp Tyr Gln His Lys Pro Gly Gln Ala Pro Arg
705                 710                 715                 720

Leu Val Ile His Gly Val Ser Asn Arg Ala Ser Gly Ile Ser Asp Arg
                725                 730                 735

Phe Ser Gly Ser Gly Ser Gly Thr Asp Phe Thr Leu Thr Ile Thr Arg
            740                 745                 750

Val Glu Pro Glu Asp Phe Ala Leu Tyr Tyr Cys Gln Val Tyr Gly Ala
            755                 760                 765

Ser Ser Tyr Thr Phe Gly Gln Gly Thr Lys Leu Glu Arg Lys
            770                 775                 780

<210> SEQ ID NO 9
<211> LENGTH: 2316
<212> TYPE: DNA
<213> ORGANISM: Artificial Sequence
<220> FEATURE:
<223> OTHER INFORMATION: chemically-synthesized gp120-ScFV construct
      comprising gp120-VRC01-ScFV -continued

```
<220> FEATURE:
<221> NAME/KEY: CDS
<222> LOCATION: (1)..(2316)

<400> SEQUENCE: 9 atg aga gtg acc gag atc aga aag tcc tac cag cat tgg tgg aga tgg      48
Met Arg Val Thr Glu Ile Arg Lys Ser Tyr Gln His Trp Trp Arg Trp
1               5                   10                  15 gga atc atg ctg ctc gga atc ctg atg atc tgc aac gcc gag gag aag      96
Gly Ile Met Leu Leu Gly Ile Leu Met Ile Cys Asn Ala Glu Glu Lys
            20                  25                  30 ctg tgg gtg acc gtg tac tac ggc gtg ccc gtg tgg aag gag gcc acc     144
Leu Trp Val Thr Val Tyr Tyr Gly Val Pro Val Trp Lys Glu Ala Thr
        35                  40                  45 acc acc ctg ttc tgc gcc agc gac cgc aag gcc tac gac acc gag gtg     192
Thr Thr Leu Phe Cys Ala Ser Asp Arg Lys Ala Tyr Asp Thr Glu Val
    50                  55                  60 cac aac gtg tgg gcc acc cac gcc tgc gtg ccc acc gac ccc aac ccc     240
His Asn Val Trp Ala Thr His Ala Cys Val Pro Thr Asp Pro Asn Pro
65                  70                  75                  80 cag gag gtg gag ctg aag aac gtg acc gag aac ttc aac atg tgg aag     288
Gln Glu Val Glu Leu Lys Asn Val Thr Glu Asn Phe Asn Met Trp Lys
                85                  90                  95 aac aac atg gtg gag cag atg cac gag gac atc atc agc ctg tgg gac     336
Asn Asn Met Val Glu Gln Met His Glu Asp Ile Ile Ser Leu Trp Asp
            100                 105                 110 cag agc ctg aag ccc tgc gtg aag ctg acc ccc ctg tgc gtg acc ctg     384
Gln Ser Leu Lys Pro Cys Val Lys Leu Thr Pro Leu Cys Val Thr Leu
        115                 120                 125 aac tgc acc gac ctg cgc aac gcc acc aac ggc aac gac acc aac acc     432
Asn Cys Thr Asp Leu Arg Asn Ala Thr Asn Gly Asn Asp Thr Asn Thr
    130                 135                 140 act agt agc agc cgc ggc atg gtg ggc ggc gag atg aag aac tgc         480
Thr Ser Ser Ser Arg Gly Met Val Gly Gly Glu Met Lys Asn Cys
145                 150                 155                 160 agc ttc aac atc acc acc aac atc cgc ggc aag gtg cag aag gag tac     528
Ser Phe Asn Ile Thr Thr Asn Ile Arg Gly Lys Val Gln Lys Glu Tyr
                165                 170                 175 gcc ctg ttc tac aag ctg gac atc gcc ccc atc gac aac aac agc aac     576
Ala Leu Phe Tyr Lys Leu Asp Ile Ala Pro Ile Asp Asn Asn Ser Asn
            180                 185                 190 aac cgc tac cgc ctg atc agc tgc aac acc agc gtg atc acc cag gcc     624
Asn Arg Tyr Arg Leu Ile Ser Cys Asn Thr Ser Val Ile Thr Gln Ala
        195                 200                 205 tgc ccc aag gtg agc ttc gag ccc atc ccc atc cac tac tgc gcc ccc     672
Cys Pro Lys Val Ser Phe Glu Pro Ile Pro Ile His Tyr Cys Ala Pro
    210                 215                 220 gcc ggc ttc gcc atc ctg aag tgc aag gac aag aag ttc aac ggc aag     720
Ala Gly Phe Ala Ile Leu Lys Cys Lys Asp Lys Lys Phe Asn Gly Lys
225                 230                 235                 240 ggc ccc tgc acc aac gtg agc acc gtg cag tgc acc cac ggc atc cgc     768
Gly Pro Cys Thr Asn Val Ser Thr Val Gln Cys Thr His Gly Ile Arg
                245                 250                 255 ccc gtg gtg agc acc cag ctg ctg ctg aac ggc agc ctg gcc gag gag     816
Pro Val Val Ser Thr Gln Leu Leu Leu Asn Gly Ser Leu Ala Glu Glu
            260                 265                 270 gag gtg gtg atc cgc agc gcc aac ttc gcc gac aac gcc aag gtg atc     864
Glu Val Val Ile Arg Ser Ala Asn Phe Ala Asp Asn Ala Lys Val Ile
        275                 280                 285
```

-continued

| | | |
|---|---|---|
| atc gtg cag ctg aac gag agc gtg gag atc aac tgc acc cgc ccc aac<br>Ile Val Gln Leu Asn Glu Ser Val Glu Ile Asn Cys Thr Arg Pro Asn<br>290               295                   300 | 912 |
| aac aac acc cgc aag tcc atc cac atc ggc ccc ggc cgc gcc ttc tac<br>Asn Asn Thr Arg Lys Ser Ile His Ile Gly Pro Gly Arg Ala Phe Tyr<br>305               310               315           320 | 960 |
| acc acc ggc gag atc atc ggc gac atc cgc cag gcc cac tgc aac ctg<br>Thr Thr Gly Glu Ile Ile Gly Asp Ile Arg Gln Ala His Cys Asn Leu<br>                        325                   330               335 | 1008 |
| agc cgc gcc aag tgg aac gac acc ctg aac aag atc gtg atc aag ctg<br>Ser Arg Ala Lys Trp Asn Asp Thr Leu Asn Lys Ile Val Ile Lys Leu<br>                340               345               350 | 1056 |
| cgc gag cag ttc ggc aac aag acc atc gtg ttc aag cac agc agc ggc<br>Arg Glu Gln Phe Gly Asn Lys Thr Ile Val Phe Lys His Ser Ser Gly<br>355               360               365 | 1104 |
| ggc gac ccc gag atc gtg acc cac agc ttc aat tgc ggc ggc gag ttc<br>Gly Asp Pro Glu Ile Val Thr His Ser Phe Asn Cys Gly Gly Glu Phe<br>370               375                   380 | 1152 |
| ttc tac tgc aac agc acc cag ctg ttc aac agc acc tgg aac gtg acc<br>Phe Tyr Cys Asn Ser Thr Gln Leu Phe Asn Ser Thr Trp Asn Val Thr<br>385               390               395           400 | 1200 |
| gag gag agc aac aac acc gtg gag aac aac acc atc acc ctg ccc tgc<br>Glu Glu Ser Asn Asn Thr Val Glu Asn Asn Thr Ile Thr Leu Pro Cys<br>                        405                   410               415 | 1248 |
| cgc atc aag cag atc atc aac atg tgg cag gag gtg ggc cgc gcc atg<br>Arg Ile Lys Gln Ile Ile Asn Met Trp Gln Glu Val Gly Arg Ala Met<br>                420               425               430 | 1296 |
| tac gcc ccc ccc atc cgc ggc cag atc cgc tgc agt tcg aac atc acc<br>Tyr Ala Pro Pro Ile Arg Gly Gln Ile Arg Cys Ser Ser Asn Ile Thr<br>435               440               445 | 1344 |
| ggc ctg ctg ctg acc cgc gac ggc ggc ccc gag gac aac aag acc gag<br>Gly Leu Leu Leu Thr Arg Asp Gly Gly Pro Glu Asp Asn Lys Thr Glu<br>450               455                   460 | 1392 |
| gtg ttc cgc ccc ggc ggc ggc gac atg cgc gac aac tgg cgc agc gag<br>Val Phe Arg Pro Gly Gly Gly Asp Met Arg Asp Asn Trp Arg Ser Glu<br>465               470                   475           480 | 1440 |
| ctg tac aag tac aag gtg gtg aag atc gag ccc ctg ggc gtg gcc ccc<br>Leu Tyr Lys Tyr Lys Val Val Lys Ile Glu Pro Leu Gly Val Ala Pro<br>                        485                   490               495 | 1488 |
| acc aag gcc aag cgc cgc gtg gtg cag cgc gag aag acc gga tcc tct<br>Thr Lys Ala Lys Arg Arg Val Val Gln Arg Glu Lys Thr Gly Ser Ser<br>                500               505               510 | 1536 |
| ggt ggt ggt ggc tcg ggc tcc gga gga ggt ggg tcg ggt ggc ggc gcg<br>Gly Gly Gly Gly Ser Gly Ser Gly Gly Gly Gly Ser Gly Gly Gly Ala<br>515               520               525 | 1584 |
| gcc gct cag gtg cag ctg gtg cag tct ggg ggt cag atg aag aag cct<br>Ala Ala Gln Val Gln Leu Val Gln Ser Gly Gly Gln Met Lys Lys Pro<br>530               535               540 | 1632 |
| ggc gag tcg atg aga att tct tgt cgg gct tct gga tat gaa ttt att<br>Gly Glu Ser Met Arg Ile Ser Cys Arg Ala Ser Gly Tyr Glu Phe Ile<br>545               550               555           560 | 1680 |
| gat tgt acg cta aat tgg att cgt ctg gcc ccc gga aaa agg cct gag<br>Asp Cys Thr Leu Asn Trp Ile Arg Leu Ala Pro Gly Lys Arg Pro Glu<br>                        565                   570               575 | 1728 |
| tgg atg gga tgg ctg aag cct cgg ggg ggg gcc gtc aac tac gca cgt<br>Trp Met Gly Trp Leu Lys Pro Arg Gly Gly Ala Val Asn Tyr Ala Arg<br>                580               585               590 | 1776 |
| cca ctt cag ggc aga gtg acc atg act cga gac gtt tat tcc gac aca<br>Pro Leu Gln Gly Arg Val Thr Met Thr Arg Asp Val Tyr Ser Asp Thr<br>595               600               605 | 1824 |

```
gcc ttt ttg gag ctg cgc tcg ttg aca gta gac gac acg gcc gtc tac       1872
Ala Phe Leu Glu Leu Arg Ser Leu Thr Val Asp Asp Thr Ala Val Tyr
610             615                 620 ttt tgt act agg gga aaa aac tgt gat tac aat tgg gac ttc gaa cac       1920
Phe Cys Thr Arg Gly Lys Asn Cys Asp Tyr Asn Trp Asp Phe Glu His
625             630                 635                 640 tgg ggc cgg ggc acc ccg gtc atc gtc tca tca gcg tcg acc ggc ggt       1968
Trp Gly Arg Gly Thr Pro Val Ile Val Ser Ser Ala Ser Thr Gly Gly
                645                 650                 655 ggc tct ggt ggc ggc ggt tcc ggt ggc ggt gga tcc gaa att gtg ttg       2016
Gly Ser Gly Gly Gly Gly Ser Gly Gly Gly Gly Ser Glu Ile Val Leu
            660                 665                 670 aca cag tct cca ggc acc ctg tct ttg tct cca ggg gaa aca gcc atc       2064
Thr Gln Ser Pro Gly Thr Leu Ser Leu Ser Pro Gly Glu Thr Ala Ile
        675                 680                 685 atc tct tgt cgg acc agt cag tat ggt tcc tta gcc tgg tat caa cag       2112
Ile Ser Cys Arg Thr Ser Gln Tyr Gly Ser Leu Ala Trp Tyr Gln Gln
690                 695                 700 agg ccc ggc cag gcc ccc agg ctc gtc atc tat tcg ggc tct act cgg       2160
Arg Pro Gly Gln Ala Pro Arg Leu Val Ile Tyr Ser Gly Ser Thr Arg
705                 710                 715                 720 gcc gct ggc atc cca gac agg ttc agc ggc agt cgg tgg ggg cca gac       2208
Ala Ala Gly Ile Pro Asp Arg Phe Ser Gly Ser Arg Trp Gly Pro Asp
                725                 730                 735 tac aat ctc acc atc agc aac ctg gag tcg gga gat ttt ggt gtt tat       2256
Tyr Asn Leu Thr Ile Ser Asn Leu Glu Ser Gly Asp Phe Gly Val Tyr
            740                 745                 750 tat tgc cag cag tat gaa ttt ttt ggc cag ggg acc aag gtc cag gtc       2304
Tyr Cys Gln Gln Tyr Glu Phe Phe Gly Gln Gly Thr Lys Val Gln Val
        755                 760                 765 gac att aag tga                                                        2316
Asp Ile Lys
770

<210> SEQ ID NO 10
<211> LENGTH: 771
<212> TYPE: PRT
<213> ORGANISM: Artificial Sequence
<220> FEATURE:
<223> OTHER INFORMATION: Synthetic Construct

<400> SEQUENCE: 10

Met Arg Val Thr Glu Ile Arg Lys Ser Tyr Gln His Trp Trp Arg Trp
1               5                   10                  15

Gly Ile Met Leu Leu Gly Ile Leu Met Ile Cys Asn Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Arg Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Glu Leu Lys Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125
```

-continued

```
Asn Cys Thr Asp Leu Arg Asn Ala Thr Asn Gly Asn Asp Thr Asn Thr
    130                 135                 140
Thr Ser Ser Arg Gly Met Val Gly Gly Glu Met Lys Asn Cys
145                 150                 155                 160
Ser Phe Asn Ile Thr Thr Asn Ile Arg Gly Lys Val Gln Lys Glu Tyr
                    165                 170                 175
Ala Leu Phe Tyr Lys Leu Asp Ile Ala Pro Ile Asp Asn Asn Ser Asn
                180                 185                 190
Asn Arg Tyr Arg Leu Ile Ser Cys Asn Thr Ser Val Ile Thr Gln Ala
            195                 200                 205
Cys Pro Lys Val Ser Phe Glu Pro Ile Pro Ile His Tyr Cys Ala Pro
210                 215                 220
Ala Gly Phe Ala Ile Leu Lys Cys Lys Asp Lys Lys Phe Asn Gly Lys
225                 230                 235                 240
Gly Pro Cys Thr Asn Val Ser Thr Val Gln Cys Thr His Gly Ile Arg
                245                 250                 255
Pro Val Val Ser Thr Gln Leu Leu Leu Asn Gly Ser Leu Ala Glu Glu
            260                 265                 270
Glu Val Val Ile Arg Ser Ala Asn Phe Ala Asp Asn Ala Lys Val Ile
        275                 280                 285
Ile Val Gln Leu Asn Glu Ser Val Glu Ile Asn Cys Thr Arg Pro Asn
290                 295                 300
Asn Asn Thr Arg Lys Ser Ile His Ile Gly Pro Gly Arg Ala Phe Tyr
305                 310                 315                 320
Thr Thr Gly Glu Ile Ile Gly Asp Ile Arg Gln Ala His Cys Asn Leu
                325                 330                 335
Ser Arg Ala Lys Trp Asn Asp Thr Leu Asn Lys Ile Val Ile Lys Leu
            340                 345                 350
Arg Glu Gln Phe Gly Asn Lys Thr Ile Val Phe Lys His Ser Ser Gly
        355                 360                 365
Gly Asp Pro Glu Ile Val Thr His Ser Phe Asn Cys Gly Gly Glu Phe
    370                 375                 380
Phe Tyr Cys Asn Ser Thr Gln Leu Phe Asn Ser Thr Trp Asn Val Thr
385                 390                 395                 400
Glu Glu Ser Asn Asn Thr Val Glu Asn Asn Thr Ile Thr Leu Pro Cys
                405                 410                 415
Arg Ile Lys Gln Ile Ile Asn Met Trp Gln Glu Val Gly Arg Ala Met
            420                 425                 430
Tyr Ala Pro Pro Ile Arg Gly Gln Ile Arg Cys Ser Ser Asn Ile Thr
        435                 440                 445
Gly Leu Leu Leu Thr Arg Asp Gly Gly Pro Glu Asp Asn Lys Thr Glu
    450                 455                 460
Val Phe Arg Pro Gly Gly Gly Asp Met Arg Asp Asn Trp Arg Ser Glu
465                 470                 475                 480
Leu Tyr Lys Tyr Lys Val Val Lys Ile Glu Pro Leu Gly Val Ala Pro
                485                 490                 495
Thr Lys Ala Lys Arg Arg Val Val Gln Arg Glu Lys Thr Gly Ser Ser
            500                 505                 510
Gly Gly Gly Gly Ser Gly Ser Gly Gly Gly Ser Gly Gly Gly Ala
        515                 520                 525
Ala Ala Gln Val Gln Leu Val Gln Ser Gly Gly Gln Met Lys Lys Pro
    530                 535                 540
```

```
Gly Glu Ser Met Arg Ile Ser Cys Arg Ala Ser Gly Tyr Glu Phe Ile
545                 550                 555                 560

Asp Cys Thr Leu Asn Trp Ile Arg Leu Ala Pro Gly Lys Arg Pro Glu
                565                 570                 575

Trp Met Gly Trp Leu Lys Pro Arg Gly Gly Ala Val Asn Tyr Ala Arg
            580                 585                 590

Pro Leu Gln Gly Arg Val Thr Met Thr Arg Asp Val Tyr Ser Asp Thr
        595                 600                 605

Ala Phe Leu Glu Leu Arg Ser Leu Thr Val Asp Asp Thr Ala Val Tyr
    610                 615                 620

Phe Cys Thr Arg Gly Lys Asn Cys Asp Tyr Asn Trp Asp Phe Glu His
625                 630                 635                 640

Trp Gly Arg Gly Thr Pro Val Ile Val Ser Ser Ala Ser Thr Gly Gly
                645                 650                 655

Gly Ser Gly Gly Gly Ser Gly Gly Gly Ser Glu Ile Val Leu
            660                 665                 670

Thr Gln Ser Pro Gly Thr Leu Ser Leu Ser Pro Gly Thr Ala Ile
        675                 680                 685

Ile Ser Cys Arg Thr Ser Gln Tyr Gly Ser Leu Ala Trp Tyr Gln Gln
690                 695                 700

Arg Pro Gly Gln Ala Pro Arg Leu Val Ile Tyr Ser Gly Ser Thr Arg
705                 710                 715                 720

Ala Ala Gly Ile Pro Asp Arg Phe Ser Gly Ser Arg Trp Gly Pro Asp
                725                 730                 735

Tyr Asn Leu Thr Ile Ser Asn Leu Glu Ser Gly Asp Phe Gly Val Tyr
            740                 745                 750

Tyr Cys Gln Gln Tyr Glu Phe Phe Gly Gln Gly Thr Lys Val Gln Val
        755                 760                 765

Asp Ile Lys
    770

<210> SEQ ID NO 11
<211> LENGTH: 2343
<212> TYPE: DNA
<213> ORGANISM: Artificial Sequence
<220> FEATURE:
<223> OTHER INFORMATION: chemically-synthesized gp120-ScFV construct
      comprising gp120-JR4-ScFV
<220> FEATURE:
<221> NAME/KEY: CDS
<222> LOCATION: (1)..(2343)

<400> SEQUENCE: 11 atg aga gtg acc gag atc aga aag tcc tac cag cat tgg tgg aga tgg    48
Met Arg Val Thr Glu Ile Arg Lys Ser Tyr Gln His Trp Trp Arg Trp
1               5                   10                  15 gga atc atg ctg ctc gga atc ctg atg atc tgc aac gcc gag gag aag    96
Gly Ile Met Leu Leu Gly Ile Leu Met Ile Cys Asn Ala Glu Glu Lys
            20                  25                  30 ctg tgg gtg acc gtg tac tac ggc gtg ccc gtg tgg aag gag gcc acc   144
Leu Trp Val Thr Val Tyr Tyr Gly Val Pro Val Trp Lys Glu Ala Thr
        35                  40                  45 acc acc ctg ttc tgc gcc agc gac cgc aag gcc tac gac acc gag gtg   192
Thr Thr Leu Phe Cys Ala Ser Asp Arg Lys Ala Tyr Asp Thr Glu Val
    50                  55                  60 cac aac gtg tgg gcc acc cac gcc tgc gtg ccc acc gac ccc aac ccc   240
His Asn Val Trp Ala Thr His Ala Cys Val Pro Thr Asp Pro Asn Pro
65                  70                  75                  80
```

-continued

| | |
|---|---|
| cag gag gtg gag ctg aag aac gtg acc gag aac ttc aac atg tgg aag<br>Gln Glu Val Glu Leu Lys Asn Val Thr Glu Asn Phe Asn Met Trp Lys<br>                85                    90                    95 | 288 |
| aac aac atg gtg gag cag atg cac gag gac atc atc agc ctg tgg gac<br>Asn Asn Met Val Glu Gln Met His Glu Asp Ile Ile Ser Leu Trp Asp<br>                100                    105                    110 | 336 |
| cag agc ctg aag ccc tgc gtg aag ctg acc ccc ctg tgc gtg acc ctg<br>Gln Ser Leu Lys Pro Cys Val Lys Leu Thr Pro Leu Cys Val Thr Leu<br>                115                    120                    125 | 384 |
| aac tgc acc gac ctg cgc aac gcc acc aac ggc aac gac acc aac acc<br>Asn Cys Thr Asp Leu Arg Asn Ala Thr Asn Gly Asn Asp Thr Asn Thr<br>130                    135                    140 | 432 |
| act agt agc agc cgc ggc atg gtg ggc ggc gag atg aag aac tgc<br>Thr Ser Ser Ser Arg Gly Met Val Gly Gly Glu Met Lys Asn Cys<br>145                    150                    155                    160 | 480 |
| agc ttc aac atc acc acc aac atc cgc ggc aag gtg cag aag gag tac<br>Ser Phe Asn Ile Thr Thr Asn Ile Arg Gly Lys Val Gln Lys Glu Tyr<br>                165                    170                    175 | 528 |
| gcc ctg ttc tac aag ctg gac atc gcc ccc atc gac aac aac agc aac<br>Ala Leu Phe Tyr Lys Leu Asp Ile Ala Pro Ile Asp Asn Asn Ser Asn<br>            180                    185                    190 | 576 |
| aac cgc tac cgc ctg atc agc tgc aac acc agc gtg atc acc cag gcc<br>Asn Arg Tyr Arg Leu Ile Ser Cys Asn Thr Ser Val Ile Thr Gln Ala<br>                195                    200                    205 | 624 |
| tgc ccc aag gtg agc ttc gag ccc atc ccc atc cac tac tgc gcc ccc<br>Cys Pro Lys Val Ser Phe Glu Pro Ile Pro Ile His Tyr Cys Ala Pro<br>210                    215                    220 | 672 |
| gcc ggc ttc gcc atc ctg aag tgc aag gac aag aag ttc aac ggc aag<br>Ala Gly Phe Ala Ile Leu Lys Cys Lys Asp Lys Lys Phe Asn Gly Lys<br>225                    230                    235                    240 | 720 |
| ggc ccc tgc acc aac gtg agc acc gtg cag tgc acc cac ggc atc cgc<br>Gly Pro Cys Thr Asn Val Ser Thr Val Gln Cys Thr His Gly Ile Arg<br>                245                    250                    255 | 768 |
| ccc gtg gtg agc acc cag ctg ctg ctg aac ggc agc ctg gcc gag gag<br>Pro Val Val Ser Thr Gln Leu Leu Leu Asn Gly Ser Leu Ala Glu Glu<br>            260                    265                    270 | 816 |
| gag gtg gtg atc cgc agc gcc aac ttc gcc gac aac gcc aag gtg atc<br>Glu Val Val Ile Arg Ser Ala Asn Phe Ala Asp Asn Ala Lys Val Ile<br>                275                    280                    285 | 864 |
| atc gtg cag ctg aac gag agc gtg gag atc aac tgc acc cgc ccc aac<br>Ile Val Gln Leu Asn Glu Ser Val Glu Ile Asn Cys Thr Arg Pro Asn<br>290                    295                    300 | 912 |
| aac aac acc cgc aag tcc atc cac atc ggc ccc ggc cgc gcc ttc tac<br>Asn Asn Thr Arg Lys Ser Ile His Ile Gly Pro Gly Arg Ala Phe Tyr<br>305                    310                    315                    320 | 960 |
| acc acc ggc gag atc atc ggc gac atc cgc cag gcc cac tgc aac ctg<br>Thr Thr Gly Glu Ile Ile Gly Asp Ile Arg Gln Ala His Cys Asn Leu<br>                325                    330                    335 | 1008 |
| agc cgc gcc aag tgg aac gac acc ctg aac aag atc gtg atc aag ctg<br>Ser Arg Ala Lys Trp Asn Asp Thr Leu Asn Lys Ile Val Ile Lys Leu<br>            340                    345                    350 | 1056 |
| cgc gag cag ttc ggc aac aag acc atc gtg ttc aag cac agc agc ggc<br>Arg Glu Gln Phe Gly Asn Lys Thr Ile Val Phe Lys His Ser Ser Gly<br>                355                    360                    365 | 1104 |
| ggc gac ccc gag atc gtg acc cac agc ttc aat tgc ggc ggc gag ttc<br>Gly Asp Pro Glu Ile Val Thr His Ser Phe Asn Cys Gly Gly Glu Phe<br>370                    375                    380 | 1152 |
| ttc tac tgc aac agc acc cag ctg ttc aac agc acc tgg aac gtg acc<br>Phe Tyr Cys Asn Ser Thr Gln Leu Phe Asn Ser Thr Trp Asn Val Thr<br>385                    390                    395                    400 | 1200 |

-continued

| | | |
|---|---|---|
| gag gag agc aac aac acc gtg gag aac aac acc atc acc ctg ccc tgc<br>Glu Glu Ser Asn Asn Thr Val Glu Asn Asn Thr Ile Thr Leu Pro Cys<br>405 410 415 | 1248 |
| cgc atc aag cag atc atc aac atg tgg cag gag gtg ggc cgc gcc atg<br>Arg Ile Lys Gln Ile Ile Asn Met Trp Gln Glu Val Gly Arg Ala Met<br>420 425 430 | 1296 |
| tac gcc ccc ccc atc cgc ggc cag atc cgc tgc agt tcg aac atc acc<br>Tyr Ala Pro Pro Ile Arg Gly Gln Ile Arg Cys Ser Ser Asn Ile Thr<br>435 440 445 | 1344 |
| ggc ctg ctg ctg acc cgc gac ggc ggc ccc gag gac aac aag acc gag<br>Gly Leu Leu Leu Thr Arg Asp Gly Gly Pro Glu Asp Asn Lys Thr Glu<br>450 455 460 | 1392 |
| gtg ttc cgc ccc ggc ggc ggc gac atg cgc gac aac tgg cgc agc gag<br>Val Phe Arg Pro Gly Gly Gly Asp Met Arg Asp Asn Trp Arg Ser Glu<br>465 470 475 480 | 1440 |
| ctg tac aag tac aag gtg gtg aag atc gag ccc ctg ggc gtg gcc ccc<br>Leu Tyr Lys Tyr Lys Val Val Lys Ile Glu Pro Leu Gly Val Ala Pro<br>485 490 495 | 1488 |
| acc aag gcc aag cgc cgc gtg gtg cag cgc gag aag acc gga tcc tct<br>Thr Lys Ala Lys Arg Arg Val Val Gln Arg Glu Lys Thr Gly Ser Ser<br>500 505 510 | 1536 |
| ggt ggc ggt ggc tcg ggc tcc gga gga ggt ggg tcg ggt ggc ggc gcg<br>Gly Gly Gly Gly Ser Gly Ser Gly Gly Gly Ser Gly Gly Gly Ala<br>515 520 525 | 1584 |
| gcc gct gag gtg cag ctg gtg gag tcg ggc cca gga ctg gtg aag cct<br>Ala Ala Glu Val Gln Leu Val Glu Ser Gly Pro Gly Leu Val Lys Pro<br>530 535 540 | 1632 |
| ttg gag act ctg tcc ctc acc tgc gct gtc cct ggt ggc tct atc aga<br>Leu Glu Thr Leu Ser Leu Thr Cys Ala Val Pro Gly Gly Ser Ile Arg<br>545 550 555 560 | 1680 |
| aga aac tac tgg agc tgg atc cgc cag ccc cca gga aag gga ctg gag<br>Arg Asn Tyr Trp Ser Trp Ile Arg Gln Pro Pro Gly Lys Gly Leu Glu<br>565 570 575 | 1728 |
| tgg att ggg cat tcc tat ggt agc gga ggt tct acc aac tac aac ccc<br>Trp Ile Gly His Ser Tyr Gly Ser Gly Gly Ser Thr Asn Tyr Asn Pro<br>580 585 590 | 1776 |
| tcc ctc gag agt cga gtc acc ctg tca gta gat acg tcc aag aat ctt<br>Ser Leu Glu Ser Arg Val Thr Leu Ser Val Asp Thr Ser Lys Asn Leu<br>595 600 605 | 1824 |
| ttc tcc ctg aag ctg acc tct gtg acc gcc gcg gac acg gcc gtt tat<br>Phe Ser Leu Lys Leu Thr Ser Val Thr Ala Ala Asp Thr Ala Val Tyr<br>610 615 620 | 1872 |
| tac tgt gcg agg acc gtc tgg tat tac act agt ggt acc cat tac ttt<br>Tyr Cys Ala Arg Thr Val Trp Tyr Tyr Thr Ser Gly Thr His Tyr Phe<br>625 630 635 640 | 1920 |
| gac cac tgg ggc cag gga gtc ctg gtc act gtc tcc tca gcg tcg acc<br>Asp His Trp Gly Gln Gly Val Leu Val Thr Val Ser Ser Ala Ser Thr<br>645 650 655 | 1968 |
| ggc ggt ggc tct ggt ggc ggc ggt tcc ggt ggc ggt gga tcc cag tct<br>Gly Gly Gly Ser Gly Gly Gly Gly Ser Gly Gly Gly Gly Ser Gln Ser<br>660 665 670 | 2016 |
| gtg ttg acg cag ccg ccc tca gtg tct gcg gcc cca ggg cag aag gtc<br>Val Leu Thr Gln Pro Pro Ser Val Ser Ala Ala Pro Gly Gln Lys Val<br>675 680 685 | 2064 |
| acc atc tcc tgc tct gga agc agc tcc aac atc ggg aga agt tat gta<br>Thr Ile Ser Cys Ser Gly Ser Ser Ser Asn Ile Gly Arg Ser Tyr Val<br>690 695 700 | 2112 |
| tct tgg tac cag cag gtc cca gga gcg gcc ccc aag ctc ctc atc tat<br>Ser Trp Tyr Gln Gln Val Pro Gly Ala Ala Pro Lys Leu Leu Ile Tyr<br>705 710 715 720 | 2160 |

| | | |
|---|---|---|
| gac act aat aag cga ccc tca ggg gtt tct gac cga ttc tct ggc tcc<br>Asp Thr Asn Lys Arg Pro Ser Gly Val Ser Asp Arg Phe Ser Gly Ser<br>              725                                 730                              735 | | 2208 |
| aag tct ggt tcc tcg gcc tcc ctg gcc atc act ggc tca caa act gga<br>Lys Ser Gly Ser Ser Ala Ser Leu Ala Ile Thr Gly Leu Gln Thr Gly<br>              740                                 745                              750 | | 2256 |
| gat gag gct gat tat tac tgc gga gca tgg gat ggc agc ctg aat gtt<br>Asp Glu Ala Asp Tyr Tyr Cys Gly Ala Trp Asp Gly Ser Leu Asn Val<br>              755                                 760                              765 | | 2304 |
| cat ata ttc gga agt ggc acc aag ttg acc gtc ctc tga<br>His Ile Phe Gly Ser Gly Thr Lys Leu Thr Val Leu<br>              770                                 775                              780 | | 2343 |

<210> SEQ ID NO 12
<211> LENGTH: 780
<212> TYPE: PRT
<213> ORGANISM: Artificial Sequence
<220> FEATURE:
<223> OTHER INFORMATION: Synthetic Construct

<400> SEQUENCE: 12

Met Arg Val Thr Glu Ile Arg Lys Ser Tyr Gln His Trp Trp Arg Trp
1               5                   10                  15

Gly Ile Met Leu Leu Gly Ile Leu Met Ile Cys Asn Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Arg Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Glu Leu Lys Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Asn Gly Asn Asp Thr Asn Thr
    130                 135                 140

Thr Ser Ser Ser Arg Gly Met Val Gly Gly Glu Met Lys Asn Cys
145                 150                 155                 160

Ser Phe Asn Ile Thr Thr Asn Ile Arg Gly Lys Val Gln Lys Glu Tyr
                165                 170                 175

Ala Leu Phe Tyr Lys Leu Asp Ile Ala Pro Ile Asp Asn Asn Ser Asn
            180                 185                 190

Asn Arg Tyr Arg Leu Ile Ser Cys Asn Thr Ser Val Ile Thr Gln Ala
        195                 200                 205

Cys Pro Lys Val Ser Phe Glu Pro Ile Pro Ile His Tyr Cys Ala Pro
    210                 215                 220

Ala Gly Phe Ala Ile Leu Lys Cys Lys Asp Lys Lys Phe Asn Gly Lys
225                 230                 235                 240

Gly Pro Cys Thr Asn Val Ser Thr Val Gln Cys Thr His Gly Ile Arg
                245                 250                 255

Pro Val Val Ser Thr Gln Leu Leu Leu Asn Gly Ser Leu Ala Glu Glu
            260                 265                 270

Glu Val Val Ile Arg Ser Ala Asn Phe Ala Asp Asn Ala Lys Val Ile
        275                 280                 285

```
Ile Val Gln Leu Asn Glu Ser Val Glu Ile Asn Cys Thr Arg Pro Asn
    290                 295                 300

Asn Asn Thr Arg Lys Ser Ile His Ile Gly Pro Gly Arg Ala Phe Tyr
305                 310                 315                 320

Thr Thr Gly Glu Ile Ile Gly Asp Ile Arg Gln Ala His Cys Asn Leu
                325                 330                 335

Ser Arg Ala Lys Trp Asn Asp Thr Leu Asn Lys Ile Val Ile Lys Leu
            340                 345                 350

Arg Glu Gln Phe Gly Asn Lys Thr Ile Val Phe Lys His Ser Ser Gly
                355                 360                 365

Gly Asp Pro Glu Ile Val Thr His Ser Phe Asn Cys Gly Gly Glu Phe
    370                 375                 380

Phe Tyr Cys Asn Ser Thr Gln Leu Phe Asn Ser Thr Trp Asn Val Thr
385                 390                 395                 400

Glu Glu Ser Asn Asn Thr Val Glu Asn Asn Thr Ile Thr Leu Pro Cys
                405                 410                 415

Arg Ile Lys Gln Ile Ile Asn Met Trp Gln Glu Val Gly Arg Ala Met
            420                 425                 430

Tyr Ala Pro Pro Ile Arg Gly Gln Ile Arg Cys Ser Ser Asn Ile Thr
                435                 440                 445

Gly Leu Leu Leu Thr Arg Asp Gly Gly Pro Glu Asp Asn Lys Thr Glu
    450                 455                 460

Val Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Thr Gly Ser Ser
            500                 505                 510

Gly Gly Gly Gly Ser Gly Ser Gly Gly Gly Ser Gly Gly Gly Ala
    515                 520                 525

Ala Ala Glu Val Gln Leu Val Glu Ser Gly Pro Gly Leu Val Lys Pro
    530                 535                 540

Leu Glu Thr Leu Ser Leu Thr Cys Ala Val Pro Gly Gly Ser Ile Arg
545                 550                 555                 560

Arg Asn Tyr Trp Ser Trp Ile Arg Gln Pro Pro Gly Lys Gly Leu Glu
                565                 570                 575

Trp Ile Gly His Ser Tyr Gly Ser Gly Gly Ser Thr Asn Tyr Asn Pro
            580                 585                 590

Ser Leu Glu Ser Arg Val Thr Leu Ser Val Asp Thr Ser Lys Asn Leu
                595                 600                 605

Phe Ser Leu Lys Leu Thr Ser Val Thr Ala Ala Asp Thr Ala Val Tyr
    610                 615                 620

Tyr Cys Ala Arg Thr Val Trp Tyr Tyr Thr Ser Gly Thr His Tyr Phe
625                 630                 635                 640

Asp His Trp Gly Gln Gly Val Leu Val Thr Val Ser Ser Ala Ser Thr
                645                 650                 655

Gly Gly Gly Ser Gly Gly Gly Ser Gly Gly Gly Ser Gln Ser
            660                 665                 670

Val Leu Thr Gln Pro Pro Ser Val Ser Ala Ala Pro Gly Gln Lys Val
    675                 680                 685

Thr Ile Ser Cys Ser Gly Ser Ser Asn Ile Gly Arg Ser Tyr Val
            690                 695                 700
```

```
Ser Trp Tyr Gln Gln Val Pro Gly Ala Ala Pro Lys Leu Leu Ile Tyr
705                 710                 715                 720

Asp Thr Asn Lys Arg Pro Ser Gly Val Ser Asp Arg Phe Ser Gly Ser
            725                 730                 735

Lys Ser Gly Ser Ser Ala Ser Leu Ala Ile Thr Gly Leu Gln Thr Gly
        740                 745                 750

Asp Glu Ala Asp Tyr Tyr Cys Gly Ala Trp Asp Gly Ser Leu Asn Val
    755                 760                 765

His Ile Phe Gly Ser Gly Thr Lys Leu Thr Val Leu
770                 775                 780

<210> SEQ ID NO 13
<211> LENGTH: 2334
<212> TYPE: DNA
<213> ORGANISM: Artificial Sequence
<220> FEATURE:
<223> OTHER INFORMATION: chemically-synthesized gp120-ScFV construct
      comprising gp120-JR48.1-ScFV
<220> FEATURE:
<221> NAME/KEY: CDS
<222> LOCATION: (1)..(2334)

<400> SEQUENCE: 13 atg aga gtg acc gag atc aga aag tcc tac cag cat tgg tgg aga tgg      48
Met Arg Val Thr Glu Ile Arg Lys Ser Tyr Gln His Trp Trp Arg Trp
1               5                   10                  15 gga atc atg ctg ctc gga atc ctg atg atc tgc aac gcc gag gag aag      96
Gly Ile Met Leu Leu Gly Ile Leu Met Ile Cys Asn Ala Glu Glu Lys
            20                  25                  30 ctg tgg gtg acc gtg tac tac ggc gtg ccc gtg tgg aag gag gcc acc     144
Leu Trp Val Thr Val Tyr Tyr Gly Val Pro Val Trp Lys Glu Ala Thr
        35                  40                  45 acc acc ctg ttc tgc gcc agc gac cgc aag gcc tac gac acc gag gtg     192
Thr Thr Leu Phe Cys Ala Ser Asp Arg Lys Ala Tyr Asp Thr Glu Val
    50                  55                  60 cac aac gtg tgg gcc acc cac gcc tgc gtg ccc acc gac ccc aac ccc     240
His Asn Val Trp Ala Thr His Ala Cys Val Pro Thr Asp Pro Asn Pro
65                  70                  75                  80 cag gag gtg gag ctg aag aac gtg acc gag aac ttc aac atg tgg aag     288
Gln Glu Val Glu Leu Lys Asn Val Thr Glu Asn Phe Asn Met Trp Lys
                85                  90                  95 aac aac atg gtg gag cag atg cac gag gac atc atc agc ctg tgg gac     336
Asn Asn Met Val Glu Gln Met His Glu Asp Ile Ile Ser Leu Trp Asp
            100                 105                 110 cag agc ctg aag ccc tgc gtg aag ctg acc ccc ctg tgc gtg acc ctg     384
Gln Ser Leu Lys Pro Cys Val Lys Leu Thr Pro Leu Cys Val Thr Leu
        115                 120                 125 aac tgc acc gac ctg cgc aac gcc acc aac ggc aac gac acc aac acc     432
Asn Cys Thr Asp Leu Arg Asn Ala Thr Asn Gly Asn Asp Thr Asn Thr
    130                 135                 140 act agt agc agc cgc ggc atg gtg ggc ggc ggc gag atg aag aac tgc     480
Thr Ser Ser Ser Arg Gly Met Val Gly Gly Gly Glu Met Lys Asn Cys
145                 150                 155                 160 agc ttc aac atc acc acc aac atc cgc ggc aag gtg cag aag gag tac     528
Ser Phe Asn Ile Thr Thr Asn Ile Arg Gly Lys Val Gln Lys Glu Tyr
                165                 170                 175 gcc ctg ttc tac aag ctg gac atc gcc ccc atc gac aac aac agc aac     576
Ala Leu Phe Tyr Lys Leu Asp Ile Ala Pro Ile Asp Asn Asn Ser Asn
            180                 185                 190
```

| | | | | | | | | | | | | | | | | |
|---|---|---|---|---|---|---|---|---|---|---|---|---|---|---|---|---|
| aac | cgc | tac | cgc | ctg | atc | agc | tgc | aac | acc | agc | gtg | atc | acc | cag | gcc | 624 |
| Asn | Arg | Tyr | Arg | Leu | Ile | Ser | Cys | Asn | Thr | Ser | Val | Ile | Thr | Gln | Ala | |
| | | | 195 | | | | 200 | | | | 205 | | | | | |
| tgc | ccc | aag | gtg | agc | ttc | gag | ccc | atc | ccc | atc | cac | tac | tgc | gcc | ccc | 672 |
| Cys | Pro | Lys | Val | Ser | Phe | Glu | Pro | Ile | Pro | Ile | His | Tyr | Cys | Ala | Pro | |
| 210 | | | | | 215 | | | | | 220 | | | | | | |
| gcc | ggc | ttc | gcc | atc | ctg | aag | tgc | aag | gac | aag | aag | ttc | aac | ggc | aag | 720 |
| Ala | Gly | Phe | Ala | Ile | Leu | Lys | Cys | Lys | Asp | Lys | Lys | Phe | Asn | Gly | Lys | |
| 225 | | | | | 230 | | | | | 235 | | | | | 240 | |
| ggc | ccc | tgc | acc | aac | gtg | agc | acc | gtg | cag | tgc | acc | cac | ggc | atc | cgc | 768 |
| Gly | Pro | Cys | Thr | Asn | Val | Ser | Thr | Val | Gln | Cys | Thr | His | Gly | Ile | Arg | |
| | | | | 245 | | | | | 250 | | | | | 255 | | |
| ccc | gtg | gtg | agc | acc | cag | ctg | ctg | ctg | aac | ggc | agc | ctg | gcc | gag | gag | 816 |
| Pro | Val | Val | Ser | Thr | Gln | Leu | Leu | Leu | Asn | Gly | Ser | Leu | Ala | Glu | Glu | |
| | | | 260 | | | | | 265 | | | | | 270 | | | |
| gag | gtg | gtg | atc | cgc | agc | gcc | aac | ttc | gcc | gac | aac | gcc | aag | gtg | atc | 864 |
| Glu | Val | Val | Ile | Arg | Ser | Ala | Asn | Phe | Ala | Asp | Asn | Ala | Lys | Val | Ile | |
| | | | | 275 | | | | | 280 | | | | | 285 | | |
| atc | gtg | cag | ctg | aac | gag | agc | gtg | gag | atc | aac | tgc | acc | cgc | ccc | aac | 912 |
| Ile | Val | Gln | Leu | Asn | Glu | Ser | Val | Glu | Ile | Asn | Cys | Thr | Arg | Pro | Asn | |
| 290 | | | | | 295 | | | | | 300 | | | | | | |
| aac | aac | acc | cgc | aag | tcc | atc | cac | atc | ggc | ccc | ggc | cgc | gcc | ttc | tac | 960 |
| Asn | Asn | Thr | Arg | Lys | Ser | Ile | His | Ile | Gly | Pro | Gly | Arg | Ala | Phe | Tyr | |
| 305 | | | | | 310 | | | | | 315 | | | | | 320 | |
| acc | acc | ggc | gag | atc | atc | ggc | gac | atc | cgc | cag | gcc | cac | tgc | aac | ctg | 1008 |
| Thr | Thr | Gly | Glu | Ile | Ile | Gly | Asp | Ile | Arg | Gln | Ala | His | Cys | Asn | Leu | |
| | | | | 325 | | | | | 330 | | | | | 335 | | |
| agc | cgc | gcc | aag | tgg | aac | gac | acc | ctg | aac | aag | atc | gtg | atc | aag | ctg | 1056 |
| Ser | Arg | Ala | Lys | Trp | Asn | Asp | Thr | Leu | Asn | Lys | Ile | Val | Ile | Lys | Leu | |
| | | | 340 | | | | | 345 | | | | | 350 | | | |
| cgc | gag | cag | ttc | ggc | aac | aag | acc | atc | gtg | ttc | aag | cac | agc | agc | ggc | 1104 |
| Arg | Glu | Gln | Phe | Gly | Asn | Lys | Thr | Ile | Val | Phe | Lys | His | Ser | Ser | Gly | |
| | | | | 355 | | | | | 360 | | | | | 365 | | |
| ggc | gac | ccc | gag | atc | gtg | acc | cac | agc | ttc | aat | tgc | ggc | ggc | gag | ttc | 1152 |
| Gly | Asp | Pro | Glu | Ile | Val | Thr | His | Ser | Phe | Asn | Cys | Gly | Gly | Glu | Phe | |
| 370 | | | | | 375 | | | | | 380 | | | | | | |
| ttc | tac | tgc | aac | agc | acc | cag | ctg | ttc | aac | agc | acc | tgg | aac | gtg | acc | 1200 |
| Phe | Tyr | Cys | Asn | Ser | Thr | Gln | Leu | Phe | Asn | Ser | Thr | Trp | Asn | Val | Thr | |
| 385 | | | | | 390 | | | | | 395 | | | | | 400 | |
| gag | gag | agc | aac | aac | acc | gtg | gag | aac | aac | acc | atc | acc | ctg | ccc | tgc | 1248 |
| Glu | Glu | Ser | Asn | Asn | Thr | Val | Glu | Asn | Asn | Thr | Ile | Thr | Leu | Pro | Cys | |
| | | | | 405 | | | | | 410 | | | | | 415 | | |
| cgc | atc | aag | cag | atc | atc | aac | atg | tgg | cag | gag | gtg | ggc | cgc | gcc | atg | 1296 |
| Arg | Ile | Lys | Gln | Ile | Ile | Asn | Met | Trp | Gln | Glu | Val | Gly | Arg | Ala | Met | |
| | | | 420 | | | | | 425 | | | | | 430 | | | |
| tac | gcc | ccc | ccc | atc | cgc | ggc | cag | atc | cgc | tgc | agt | tcg | aac | atc | acc | 1344 |
| Tyr | Ala | Pro | Pro | Ile | Arg | Gly | Gln | Ile | Arg | Cys | Ser | Ser | Asn | Ile | Thr | |
| | | | | 435 | | | | | 440 | | | | | 445 | | |
| ggc | ctg | ctg | ctg | acc | cgc | gac | ggc | ggc | ccc | gag | gac | aac | aag | acc | gag | 1392 |
| Gly | Leu | Leu | Leu | Thr | Arg | Asp | Gly | Gly | Pro | Glu | Asp | Asn | Lys | Thr | Glu | |
| 450 | | | | | 455 | | | | | 460 | | | | | | |
| gtg | ttc | cgc | ccc | ggc | ggc | ggc | gac | atg | cgc | gac | aac | tgg | cgc | agc | gag | 1440 |
| Val | Phe | Arg | Pro | Gly | Gly | Gly | Asp | Met | Arg | Asp | Asn | Trp | Arg | Ser | Glu | |
| 465 | | | | | 470 | | | | | 475 | | | | | 480 | |
| ctg | tac | aag | tac | aag | gtg | gtg | aag | atc | gag | ccc | ctg | ggc | gtg | gcc | ccc | 1488 |
| Leu | Tyr | Lys | Tyr | Lys | Val | Val | Lys | Ile | Glu | Pro | Leu | Gly | Val | Ala | Pro | |
| | | | 485 | | | | | 490 | | | | | 495 | | | |
| acc | aag | gcc | aag | cgc | cgc | gtg | gtg | cag | cgc | gag | aag | acc | gga | tcc | tct | 1536 |
| Thr | Lys | Ala | Lys | Arg | Arg | Val | Val | Gln | Arg | Glu | Lys | Thr | Gly | Ser | Ser | |
| | | | | 500 | | | | | 505 | | | | | 510 | | |

```
ggt ggc ggt ggc tcg ggc tcc gga gga ggt ggg tcg ggt ggc ggc gcg        1584
Gly Gly Gly Gly Ser Gly Ser Gly Gly Gly Ser Gly Gly Gly Ala
            515                 520                 525 gcc gct gag gtg cag ctg gtg gag tct ggg gga ggc gtg gtc cag cct        1632
Ala Ala Glu Val Gln Leu Val Glu Ser Gly Gly Gly Val Val Gln Pro
530                 535                 540 ggg agg tcc ctg aga ctc tcc tgt gca gcc tct gga ttc acc ttc agt        1680
Gly Arg Ser Leu Arg Leu Ser Cys Ala Ala Ser Gly Phe Thr Phe Ser
545                 550                 555                 560 agc tct ggc atg aac tgg gtc cgc cag gct cca ggc aag ggg ctg gag        1728
Ser Ser Gly Met Asn Trp Val Arg Gln Ala Pro Gly Lys Gly Leu Glu
                565                 570                 575 tgg gtg gca att ata tca tat gat gga agt aat aaa tat tat gca gcc        1776
Trp Val Ala Ile Ile Ser Tyr Asp Gly Ser Asn Lys Tyr Tyr Ala Ala
            580                 585                 590 tcc gtg aag ggc cga ttc acc atc tcc aga gac att tcc aag aac atc        1824
Ser Val Lys Gly Arg Phe Thr Ile Ser Arg Asp Ile Ser Lys Asn Ile
        595                 600                 605 ctg ttt ctg caa atg aac agc ctg aga gct gat gac acg gct gtg tat        1872
Leu Phe Leu Gln Met Asn Ser Leu Arg Ala Asp Asp Thr Ala Val Tyr
610                 615                 620 tac tgt aca agg ggt gta gca gtg gcg gga ccc ggc tgg aac tgg ttc        1920
Tyr Cys Thr Arg Gly Val Ala Val Ala Gly Pro Gly Trp Asn Trp Phe
625                 630                 635                 640 gac ccc tgg ggc cag gga acc ctg gtc acc gtc tca gcg tcg acc            1968
Asp Pro Trp Gly Gln Gly Thr Leu Val Thr Val Ser Ala Ser Thr
                645                 650                 655 ggc ggt ggc tct ggt ggc ggt tcc ggt ggc ggt gga tcc gat att            2016
Gly Gly Gly Ser Gly Gly Gly Ser Gly Gly Gly Gly Ser Asp Ile
            660                 665                 670 gtg atg act cag tct cca tcc tcc ctg tct gca tct gtg gga gac aga        2064
Val Met Thr Gln Ser Pro Ser Ser Leu Ser Ala Ser Val Gly Asp Arg
        675                 680                 685 gtc acc atc act tgc cgg gca agt cag agg att agc agc ttt tta aat        2112
Val Thr Ile Thr Cys Arg Ala Ser Gln Arg Ile Ser Ser Phe Leu Asn
690                 695                 700 tgg tat cag cag aaa cca ggg aaa gcc cct aag gtc ctg atc tat gct        2160
Trp Tyr Gln Gln Lys Pro Gly Lys Ala Pro Lys Val Leu Ile Tyr Ala
705                 710                 715                 720 gca tcc agt ttg caa agt ggg gtc ccc tca agg ttc agt ggc agt gga        2208
Ala Ser Ser Leu Gln Ser Gly Val Pro Ser Arg Phe Ser Gly Ser Gly
                725                 730                 735 tct ggg aca gat ttc act ctc acc atc agc agt ctg caa cct gaa gac        2256
Ser Gly Thr Asp Phe Thr Leu Thr Ile Ser Ser Leu Gln Pro Glu Asp
            740                 745                 750 ttt gcg act tac tac tgt caa cag act tac agt ctc ccg ctc act ttc        2304
Phe Ala Thr Tyr Tyr Cys Gln Gln Thr Tyr Ser Leu Pro Leu Thr Phe
        755                 760                 765 ggc gga ggg acc aag gta gag atc aaa tga                                2334
Gly Gly Gly Thr Lys Val Glu Ile Lys
    770                 775
```

<210> SEQ ID NO 14
<211> LENGTH: 777
<212> TYPE: PRT
<213> ORGANISM: Artificial Sequence
<220> FEATURE:
<223> OTHER INFORMATION: Synthetic Construct

<400> SEQUENCE: 14

```
Met Arg Val Thr Glu Ile Arg Lys Ser Tyr Gln His Trp Trp Arg Trp
1               5                   10                  15
Gly Ile Met Leu Leu Gly Ile Leu Met Ile Cys Asn Ala Glu Glu Lys
            20                  25                  30
Leu Trp Val Thr Val Tyr Tyr Gly Val Pro Val Trp Lys Glu Ala Thr
        35                  40                  45
Thr Thr Leu Phe Cys Ala Ser Asp Arg Lys Ala Tyr Asp Thr Glu Val
50                  55                  60
His Asn Val Trp Ala Thr His Ala Cys Val Pro Thr Asp Pro Asn Pro
65                  70                  75                  80
Gln Glu Val Glu Leu Lys Asn Val Thr Glu Asn Phe Asn Met Trp Lys
                85                  90                  95
Asn Asn Met Val Glu Gln Met His Glu Asp Ile Ile Ser Leu Trp Asp
            100                 105                 110
Gln Ser Leu Lys Pro Cys Val Lys Leu Thr Pro Leu Cys Val Thr Leu
        115                 120                 125
Asn Cys Thr Asp Leu Arg Asn Ala Thr Asn Gly Asn Asp Thr Asn Thr
130                 135                 140
Thr Ser Ser Ser Arg Gly Met Val Gly Gly Glu Met Lys Asn Cys
145                 150                 155                 160
Ser Phe Asn Ile Thr Thr Asn Ile Arg Gly Lys Val Gln Lys Glu Tyr
                165                 170                 175
Ala Leu Phe Tyr Lys Leu Asp Ile Ala Pro Ile Asp Asn Asn Ser Asn
            180                 185                 190
Asn Arg Tyr Arg Leu Ile Ser Cys Asn Thr Ser Val Ile Thr Gln Ala
        195                 200                 205
Cys Pro Lys Val Ser Phe Glu Pro Ile Pro Ile His Tyr Cys Ala Pro
210                 215                 220
Ala Gly Phe Ala Ile Leu Lys Cys Lys Asp Lys Lys Phe Asn Gly Lys
225                 230                 235                 240
Gly Pro Cys Thr Asn Val Ser Thr Val Gln Cys Thr His Gly Ile Arg
                245                 250                 255
Pro Val Val Ser Thr Gln Leu Leu Asn Gly Ser Leu Ala Glu Glu
            260                 265                 270
Glu Val Val Ile Arg Ser Ala Asn Phe Ala Asp Asn Ala Lys Val Ile
        275                 280                 285
Ile Val Gln Leu Asn Glu Ser Val Glu Ile Asn Cys Thr Arg Pro Asn
290                 295                 300
Asn Asn Thr Arg Lys Ser Ile His Ile Gly Pro Gly Arg Ala Phe Tyr
305                 310                 315                 320
Thr Thr Gly Glu Ile Ile Gly Asp Ile Arg Gln Ala His Cys Asn Leu
                325                 330                 335
Ser Arg Ala Lys Trp Asn Asp Thr Leu Asn Lys Ile Val Ile Lys Leu
            340                 345                 350
Arg Glu Gln Phe Gly Asn Lys Thr Ile Val Phe Lys His Ser Ser Gly
        355                 360                 365
Gly Asp Pro Glu Ile Val Thr His Ser Phe Asn Cys Gly Gly Glu Phe
370                 375                 380
Phe Tyr Cys Asn Ser Thr Gln Leu Phe Asn Ser Thr Trp Asn Val Thr
385                 390                 395                 400
```

```
Glu Glu Ser Asn Asn Thr Val Glu Asn Asn Thr Ile Thr Leu Pro Cys
                405                 410                 415
Arg Ile Lys Gln Ile Ile Asn Met Trp Gln Glu Val Gly Arg Ala Met
            420                 425                 430
Tyr Ala Pro Pro Ile Arg Gly Gln Ile Arg Cys Ser Ser Asn Ile Thr
        435                 440                 445
Gly Leu Leu Leu Thr Arg Asp Gly Pro Glu Asp Asn Lys Thr Glu
    450                 455                 460
Val Phe Arg Pro Gly Gly Asp Met Arg Asp Asn Trp Arg Ser Glu
465                 470                 475                 480
Leu Tyr Lys Tyr Lys Val Val Lys Ile Glu Pro Leu Gly Val Ala Pro
            485                 490                 495
Thr Lys Ala Lys Arg Arg Val Val Gln Arg Glu Lys Thr Gly Ser Ser
        500                 505                 510
Gly Gly Gly Gly Ser Gly Ser Gly Gly Gly Ser Gly Gly Gly Ala
    515                 520                 525
Ala Ala Glu Val Gln Leu Val Glu Ser Gly Gly Val Val Gln Pro
    530                 535                 540
Gly Arg Ser Leu Arg Leu Ser Cys Ala Ala Ser Gly Phe Thr Phe Ser
545                 550                 555                 560
Ser Ser Gly Met Asn Trp Val Arg Gln Ala Pro Gly Lys Gly Leu Glu
            565                 570                 575
Trp Val Ala Ile Ile Ser Tyr Asp Gly Ser Asn Lys Tyr Tyr Ala Ala
        580                 585                 590
Ser Val Lys Gly Arg Phe Thr Ile Ser Arg Asp Ile Ser Lys Asn Ile
            595                 600                 605
Leu Phe Leu Gln Met Asn Ser Leu Arg Ala Asp Asp Thr Ala Val Tyr
    610                 615                 620
Tyr Cys Thr Arg Gly Val Ala Val Ala Gly Pro Gly Trp Asn Trp Phe
625                 630                 635                 640
Asp Pro Trp Gly Gln Gly Thr Leu Val Thr Val Ser Ser Ala Ser Thr
            645                 650                 655
Gly Gly Gly Ser Gly Gly Gly Ser Gly Gly Gly Ser Asp Ile
        660                 665                 670
Val Met Thr Gln Ser Pro Ser Ser Leu Ser Ala Ser Val Gly Asp Arg
    675                 680                 685
Val Thr Ile Thr Cys Arg Ala Ser Gln Arg Ile Ser Ser Phe Leu Asn
    690                 695                 700
Trp Tyr Gln Gln Lys Pro Gly Lys Ala Pro Lys Val Leu Ile Tyr Ala
705                 710                 715                 720
Ala Ser Ser Leu Gln Ser Gly Val Pro Ser Arg Phe Ser Gly Ser Gly
            725                 730                 735
Ser Gly Thr Asp Phe Thr Leu Thr Ile Ser Ser Leu Gln Pro Glu Asp
        740                 745                 750
Phe Ala Thr Tyr Tyr Cys Gln Gln Thr Tyr Ser Leu Pro Leu Thr Phe
        755                 760                 765
Gly Gly Gly Thr Lys Val Glu Ile Lys
    770                 775
```

<210> SEQ ID NO 15
<211> LENGTH: 693
<212> TYPE: PRT
<213> ORGANISM: Human immunodeficiency virus type 1

<400> SEQUENCE: 15

```
Met Arg Val Thr Glu Ile Arg Lys Ser Tyr Gln His Trp Trp Arg Trp
1               5                   10                  15

Gly Ile Met Leu Leu Gly Ile Leu Met Ile Cys Asn Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Arg Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Glu Leu Lys Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Asn Gly Asn Asp Thr Asn Thr
    130                 135                 140

Thr Ser Ser Ser Arg Gly Met Val Gly Gly Glu Met Lys Asn Cys
145                 150                 155                 160

Ser Phe Asn Ile Thr Thr Asn Ile Arg Gly Lys Val Gln Lys Glu Tyr
                165                 170                 175

Ala Leu Phe Tyr Lys Leu Asp Ile Ala Pro Ile Asp Asn Asn Ser Asn
            180                 185                 190

Asn Arg Tyr Arg Leu Ile Ser Cys Asn Thr Ser Val Ile Thr Gln Ala
        195                 200                 205

Cys Pro Lys Val Ser Phe Glu Pro Ile Pro Ile His Tyr Cys Ala Pro
    210                 215                 220

Ala Gly Phe Ala Ile Leu Lys Cys Lys Asp Lys Lys Phe Asn Gly Lys
225                 230                 235                 240

Gly Pro Cys Thr Asn Val Ser Thr Val Gln Cys Thr His Gly Ile Arg
                245                 250                 255

Pro Val Val Ser Thr Gln Leu Leu Leu Asn Gly Ser Leu Ala Glu Glu
            260                 265                 270

Glu Val Val Ile Arg Ser Ala Asn Phe Ala Asp Asn Ala Lys Val Ile
        275                 280                 285

Ile Val Gln Leu Asn Glu Ser Val Glu Ile Asn Cys Thr Arg Pro Asn
    290                 295                 300

Asn Asn Thr Arg Lys Ser Ile His Ile Gly Pro Gly Arg Ala Phe Tyr
305                 310                 315                 320

Thr Thr Gly Glu Ile Ile Gly Asp Ile Arg Gln Ala His Cys Asn Leu
                325                 330                 335

Ser Arg Ala Lys Trp Asn Asp Thr Leu Asn Lys Ile Val Ile Lys Leu
            340                 345                 350

Arg Glu Gln Phe Gly Asn Lys Thr Ile Val Phe Lys His Ser Ser Gly
        355                 360                 365

Gly Asp Pro Glu Ile Val Thr His Ser Phe Asn Cys Gly Gly Glu Phe
    370                 375                 380

Phe Tyr Cys Asn Ser Thr Gln Leu Phe Asn Ser Thr Trp Asn Val Thr
385                 390                 395                 400

Glu Glu Ser Asn Asn Thr Val Glu Asn Asn Thr Ile Thr Leu Pro Cys
                405                 410                 415
```

```
Arg Ile Lys Gln Ile Ile Asn Met Trp Gln Glu Val Gly Arg Ala Met
            420                 425                 430

Tyr Ala Pro Pro Ile Arg Gly Gln Ile Arg Cys Ser Ser Asn Ile Thr
    435                 440                 445

Gly Leu Leu Leu Thr Arg Asp Gly Gly Pro Glu Asp Asn Lys Thr Glu
450                 455                 460

Val Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Val Phe Leu Gly Phe Leu Gly Ala Ala Gly Ser Thr Met
            515                 520                 525

Gly Ala Ala Ala Met Thr Leu Thr Val Gln Ala Arg Leu Leu Leu Ser
530                 535                 540

Gly Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Ala Val Pro Trp
            595                 600                 605

Asn Ala Ser Trp Ser Asn Lys Ser Leu Asn Lys Ile Trp Asp Asn Met
610                 615                 620

Thr Trp Ile Glu Trp Asp Arg Glu Ile Asn Asn Tyr Thr Ser Ile Ile
625                 630                 635                 640

Tyr Ser Leu Ile Glu Glu Ser Gln Asn Gln Gln Glu Lys Asn Glu Gln
                645                 650                 655

Glu Leu Leu Glu Leu Asp Lys Trp Ala Ser Leu Trp Asn Trp Phe Asp
            660                 665                 670

Ile Thr Lys Trp Leu Trp Tyr Ile Lys Ile Phe Ile Met Ile Val Gly
            675                 680                 685

Gly Leu Ile Gly Leu
    690

<210> SEQ ID NO 16
<211> LENGTH: 21
<212> TYPE: PRT
<213> ORGANISM: Artificial Sequence
<220> FEATURE:
<223> OTHER INFORMATION: GSA linker sequence

<400> SEQUENCE: 16

Gly Ser Ser Gly Gly Gly Gly Ser Gly Gly Gly Gly Ser Gly
1               5                   10                  15

Gly Gly Ala Ala Ala
            20

<210> SEQ ID NO 17
<211> LENGTH: 15
<212> TYPE: PRT
<213> ORGANISM: Artificial Sequence
<220> FEATURE:
<223> OTHER INFORMATION: GS linker sequence
```

```
<400> SEQUENCE: 17

Gly Gly Gly Gly Ser Gly Gly Gly Gly Ser Gly Gly Gly Gly Ser
1               5                   10                  15
```

RECOMBINANT FUSION PROTEIN COMPRISING HIV GP120 LINKED TO AN ENHANCING CD4 BINDING SITE MAB

STATEMENT OF FEDERALLY SPONSORED RESEARCH AND DEVELOPMENT

This invention was made with government support under Grant Numbers AI087181, AI084830, CA149196 and AI084580 awarded by the NIH. The government has certain rights in the invention.

TECHNICAL FIELD

The present invention is directed to the fields of immunology and virology. More particularly, the invention is directed to novel fusion proteins that may serve in immunogenic formulations against HIV-1 infection and to a novel broadly neutralizing antibody that may serve in the prevention and/or treatment of HIV-1 infections in a subject.

BACKGROUND OF INVENTION

It is well established that neutralizing antibodies (nAbs) against the HIV-1 envelope protein (Env) can be protective, as was demonstrated by passive immunization studies in non-human primates [1-3]. Therefore, the isolation of broadly nAbs (bnAbs) that can neutralize diversified HIV-1 strains is being pursued as a major path to the rational design of an effective HIV-1 vaccine [4].

Large numbers of potent new bnAbs have been recently isolated from multiple donors [5-11], mainly due to new technologies for isolating human monoclonal antibodies (mAbs) and the employment of a high-throughput neutralization screen system [5, 12-15]. Four types of new potent HIV-1 bnAbs have been identified. 1) The newly isolated 'VRC01-like' bnAbs [7, 8, 10] can block Env binding to primary receptor CD4 and they are superior to the previous CD4 binding site (CD4bs) nAb b12 [16]. 2) The newly isolated PGT series bnAbs [9] are glycan dependent and much more potent and broadly active than the old glycan-dependent nAb 2G12 [17], which can block Env binding to co-receptor CCR5. 3) The so-called 'PG9-like' bnAbs bind conserved conformational epitopes on the Env trimer of HIV-1 involving the V1/V2 and V3 regions and glycan, including PG9, PG16 [5] and CH01~04 [11]. They are superior in breadth compared to previously identified strain-specific potent nAbs that recognize quaternary neutralizing epitopes (QNE) of HIV-1 Env [18, 19]. 4) The new isolated bnAb 10E8 targets the membrane proximal external region (MPER) of gp41 and is much more potent and broadly active than the old MPER nAbs 2F5 and 4E10 (J. Huang et al., *Nature* (2012) 491: 406-412).

These new bnAbs collectively neutralize the majority of the highly diversified HIV-1 strains [9]. However, these bnAbs also demonstrate some unusual features that may be major roadblocks for HIV-1 vaccine development. These highly mutated bnAbs were isolated from rare (<3%) "elite neutralizers" that were selected from more than a thousand HIV-1-infected persons [5, 11, 15]. Compared with the degree of somatic mutation in other Ab responses [13, 20], a common feature of these HIV-1 bnAbs is their apparent unusually high levels of mutation, especially in the heavy chain V (VH) genes [5-11]. This high level of mutation raises a high bar for a vaccine to generate this type of Ab response, which may be a major hurdle for HIV-1 vaccine development. In addition, some of these bnAbs showed auto/poly-reactivity [7, 8, 10], which is detrimental for B cell response. Currently, no HIV-1 vaccine candidates can elicit bnAb responses [4].

Thus, there continues to be a great need for HIV-1 vaccine candidates that can elicit bnAb responses, as well as potent HIV-1 bnAbs with improved characteristics.

BRIEF SUMMARY OF INVENTION

The present invention provides (i) fusion protein immunogens comprising a common transitional conformation structure of HIV-1 Env that may be used in vaccine formulations, and (ii) an HIV-1 broadly neutralizing human monoclonal antibody (N60-B1.1). In additional, the invention provides vaccine formulations, and methods of utilizing the Env immunogens and the antibody in a variety of manners.

In a first embodiment, the present invention is directed to fusion proteins comprising a portion of the HIV-1 Env polypeptide and single-chain fragment V regions of enhancing antibodies. These Env fusion proteins include: gp120-b12-ScFV, gp120-VRC01-ScFV, gp120-JR4-ScFV and gp120-JR48.1-ScFV. Thus, in aspects of this embodiment, the invention is directed to: the gp120-b12-ScFV polypeptide comprising the amino acid sequence set forth in SEQ ID NO:8; the gp120-VRC01-ScFV polypeptide comprising the amino acid sequence set forth in SEQ ID NO:10; the gp120-JR4-ScFV polypeptide comprising the amino acid sequence set forth in SEQ ID NO:12; and the gp120-JR48.1-ScFV polypeptide comprising the amino acid sequence set forth in SEQ ID NO:14.

In related aspects, the invention is directed to: the polynucleotide sequence encoding the gp120-b12-ScFV polypeptide set forth in SEQ ID NO:7; the polynucleotide sequence encoding the gp120-VRC01-ScFV polypeptide set forth in SEQ ID NO:9; the polynucleotide sequence encoding the gp120-JR4-ScFV polypeptide set forth in SEQ ID NO:11; and the polynucleotide sequence encoding the gp120-JR48.1-ScFV polypeptide set forth in SEQ ID NO:13.

In further related aspects, the invention is directed to variants of gp120-b12-ScFV, gp120-VRC01-ScFV, gp120-JR4-ScFV and gp120-JR48.1-ScFV. For example, the present invention encompasses: a variant having at least about 95% sequence identity over the full length of the gp120-b12-ScFV polypeptide as set forth in SEQ ID NO:8; a variant having at least about 95% sequence identity over the full length of the gp120-VRC01-ScFV polypeptide as set forth in SEQ ID NO:10; a variant having at least about 95% sequence identity over the full length of the gp120-JR4-ScFV polypeptide as set forth in SEQ ID NO:12; and a variant having at least about 95% sequence identity over the full length of the gp120-JR48.1-ScFV polypeptide as set forth in SEQ ID NO:14. As another example, the invention encompasses variants having at least about 95% sequence identity within only one or two of the domains of the gp120-b12-ScFV, gp120-VRC01-ScFV, gp120-JR4-ScFV and gp120-JR48.1-ScFV polypeptides. For example, the amino acid changes may be limited to one or more of: (i) the HIV-1 Env peptide domain of the polypeptide, (ii) the linker domain of the polypeptide, and (iii) the ScFV domain of the polypeptide. In each of the variants, the amino acid changes may be one or more of additions, substitutions or deletions, and the type of changes may vary by the domain of a particular variant polypeptide.

In a second embodiment, the present invention is directed to immunogenic formulations comprising one or more of the Env fusion protein immunogens gp120-b12-ScFV, gp120-

VRC01-ScFV, gp120-JR4-ScFV and gp120-JR48.1-ScFV, one or more variants thereof, and a pharmaceutically acceptable carrier and/or adjuvant. Thus, in one aspect, the invention is directed to an immunogenic formulation comprising: (a) one or more of the polypeptides gp120-b12-ScFV (SEQ ID NO:8), gp120-VRC01-ScFV (SEQ ID NO:10), gp120-JR4-ScFV (SEQ ID NO:12) and gp120-JR48.1-ScFV (SEQ ID NO:14) and a pharmaceutically acceptable carrier and/or adjuvant, or (b) the formulation of (a) wherein at least one of the polypeptides is a variant and wherein the variant has at least about 95% sequence identity with the full length reference sequence. In related aspects, the invention is directed to an immunogenic formulation comprising two or more of the polypeptides or variants thereof, three or more of the polypeptides or variants thereof, and each of the polypeptides or variants thereof. In an exemplary, but not limiting aspect, the invention is directed to an immunogenic formulation comprising each of the polypeptides gp120-b12-ScFV (SEQ ID NO:8), gp120-VRC01-ScFV (SEQ ID NO:10), gp120-JR4-ScFV (SEQ ID NO:12) and gp120-JR48.1-ScFV (SEQ ID NO:14) and a pharmaceutically acceptable carrier and/or adjuvant.

In a third embodiment, the invention is directed to methods of using the Env fusion protein immunogens gp120-b12-ScFV, gp120-VRC01-ScFV, gp120-JR4-ScFV and gp120-JR48.1-ScFV, variants thereof, and immunogenic formulations comprising the polypeptides and variants in all possible combinations in the generation of an immune response in a subject. In one aspect of this embodiment, the invention is directed to a method of generating an immune response in a subject comprising administering an immunologically effective amount of an immunogenic formulation as defined herein to a subject, thereby generating an immune response in a subject. In a related aspect, the invention is directed to a method of generating a protective immune response in a subject comprising administering an immunologically effective amount of an immunogenic formulation as defined herein to a subject, thereby generating a protective immune response in a subject.

In a fourth embodiment, the present invention is directed to a novel antibody that exhibits binding specificity for the HIV-1 Env polypeptide. This antibody, termed N60-B1.1 herein, comprises a VK domain having the amino acid sequence set forth in SEQ ID NO:2 and a VH domain having the amino acid sequence set forth in SEQ ID NO:4. The invention is also directed to fragments of N60-B1.1 that maintain the ability to bind the HIV-1 Env polypeptide.

In one aspect of this embodiment, the invention is directed to an isolated antibody or an HIV-1 Env protein binding fragment thereof, wherein the antibody comprises: (a) a VK domain comprising the amino acid sequence of SEQ ID NO:2, (b) a VH domain comprising the amino acid sequence of SEQ ID NO:4, (c) a VK domain comprising an amino acid sequence with at least about 95% sequence identity to SEQ ID NO:2, or (d) a VH domain comprising an amino acid sequence with at least about 95% sequence identity to SEQ ID NO:4. In particular aspects, the invention is directed to (i) an isolated antibody or an HIV-1 Env protein binding fragment thereof wherein the antibody comprises a VK domain having the amino acid sequence of SEQ ID NO:2 and a VH domain having the amino acid sequence of SEQ ID NO:4; (ii) an isolated antibody or an HIV-1 Env protein binding fragment thereof wherein the antibody comprises a VK domain comprising the amino acid sequence of SEQ ID NO:2 and a VH domain comprising an amino acid sequence with at least about 95% sequence identity to SEQ ID NO:4; (iii) an isolated antibody or an HIV-1 Env protein binding fragment thereof wherein the antibody comprises a VK domain comprising an amino acid sequence with at least about 95% sequence identity to SEQ ID NO:2 and a VH domain comprising the amino acid sequence of SEQ ID NO:4; and (iv) an isolated antibody or an HIV-1 Env protein binding fragment thereof wherein the antibody comprises a VK domain comprising an amino acid sequence with at least about 95% sequence identity to SEQ ID NO:2 and a VH domain comprising an amino acid sequence with at least about 95% sequence identity to SEQ ID NO:4.

This embodiment of the invention includes an isolated antibody or an HIV-1 Env protein binding fragment thereof wherein the VK domain comprises amino acids 1-95 of SEQ ID NO:2 or the VH domain comprises amino acids 1-102 of SEQ ID NO:4, as well as an isolated antibody or an HIV-1 Env protein binding fragment thereof wherein the VK domain comprises amino acids 1-95 of SEQ ID NO:2 and the VH domain comprises amino acids 1-102 of SEQ ID NO:4.

In exemplary, but not limiting aspects of this embodiment, the antibodies have binding specificity for HIV-1 Env protein; the antibody is a fully human antibody or a chimeric antibody; the antibody is a monoclonal antibody; the antibody is a recombinant antibody.

In aspects of this embodiment directed to the HIV-1 Env protein binding fragments of the antibodies, the fragment may be, but is not limited to, a Fab fragment, F(ab')$_2$ fragment, and single chain Fv (scFv).

This embodiment includes pharmaceutical formulations comprising the antibodies and/or HIV-1 Env protein binding fragments thereof and a pharmaceutically acceptable carrier.

In a fifth embodiment, the present invention is directed to engineered bi- and tri-specific antibodies. Such engineered antibodies have binding affinity for two or even three different epitopes. The antigen binding domains of two or three different antibodies can be combined on a constant region frame to create bi- and tri-specific antibodies. As an example, the antigen binding domains of the following antibodies can be used: (i) bnAbs against glycan-dependent V1V2 and V3 related regions, e.g., N60-B1.1, PG9 and PGT128; (ii) bnAbs against CD4bs, e.g., b12 and VRC01; (iii) ADCC antibodies against the cluster A region of gp120, e.g., JR4 and JR48.1. The creation and use of such bi- and tri-specific antibodies permit simultaneous and synergetic binding to gp120, for example.

In a sixth embodiment, the invention is directed to methods of using antibodies and fragments thereof in the treatment or prevention of HIV-1 infection in a subject. Thus, in one aspect the invention is directed to a method of preventing an HIV-1 infection in a subject, comprising administering a therapeutically effective amount of a pharmaceutical formulation comprising one or more of the antibodies and antibodies fragments as defined herein to a subject at risk of developing an HIV-1 infection, thereby inhibiting an HIV-1 infection in a subject. In a related aspect, the invention is directed to a method of treating an HIV-1 infection in a subject, comprising administering a therapeutically effective amount of a pharmaceutical formulation comprising one or more of the antibodies and antibodies fragments as defined herein to a subject having an HIV-1 infection, thereby treating an HIV-1 infection in a subject.

The foregoing has outlined rather broadly the features and technical advantages of the present invention in order that the detailed description of the invention that follows may be better understood. Additional features and advantages of the invention will be described herein, which form the subject matter of the claims of the invention.

BRIEF DESCRIPTION OF DRAWINGS

FIG. 1. A sequence alignment of the light (VK) and heavy (VH) chain variable regions of clones N60-B1.1, N60-B1.2 (HGKV3-15*01) and IGHV4-39*01 is provided. The VK chain of N60-B1.1 comprises amino acids 1-95 of SEQ ID NO:2. The amino acid sequence of the N60-B1.2 (HGKV3-15*01) VK chain (un-mutated germline VK) is provided in SEQ ID NO:5. The VH chain of N60-B1.1 comprises amino acids 1-102 of SEQ ID NO:4. The amino acid sequence of the IGHV4-39*01 VH chain (un-mutated germline VH) is provided in SEQ ID NO:6. Non-matching residues are shown in bold below the lower sequences of the alignments. The framework (FR) and cluster complementarity determining regions (CDRs) are indicated above the alignments.

FIG. 2. The results of a comparison of the binding abilities of several different antibodies to monomeric gp120 and variants thereof are provided. The variants include those having mutations in the V1/V2 loop (dV1V2), those having mutations in the co-receptor binding site (CoRbs, I420R), and those having mutations in the V3 loop (dV3). In addition to N60-B1.1, antibodies of the clones N60-B1.2, 697-3D, b12, 17b, and N12-O3.1.

FIGS. 3A-C. The four panels of FIG. 3A demonstrate the lack of N60-B1.1 auto-reactivity where the antibody was cultured with dsDNA, insulin, ssDNA and lipopolysaccharide (LPS) and compared to the bnAbs 4E10, 2F5, PG9 and PG16. FIG. 3B illustrates the in vivo protective effect of N60-B1.1 in a rhesus macaque model. FIG. 3C provides results demonstrating that sterilizing immunity against the intra-rectal challenge of SHIV162P3 can be achieved in the rhesus macaque model.

FIG. 4A-C. The three panels in the figure show the results of competition binding studies of N60-B1.1 and other antibodies against gp120.

FIG. 5. The four panels illustrate the enhanced exposure of bnAb epitopes in gp120-ScFv fusion proteins.

FIG. 6. The four panels illustrate the enhanced exposure of ADCC Ab epitopes in gp120-b12/VRC01 ScFv fusion proteins.

FIG. 7. This figure provides examples of bi- and tri-specific HIV-1 protective Abs.

DETAILED DESCRIPTION OF THE INVENTION

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As suggested above, the present invention is based on the discovery by the inventors of the broadly neutralizing antibody (nAb) N60-B1.1 that exhibits binding specificity to the HIV-1 envelope protein (Env). Through the diligent efforts of the inventors to characterize this antibody, it was found, as shown below, that the antibody has protective activity in a passive immunization study in non-human primates. Characterization of the antibody further led the inventors to prepare four different fusion proteins that comprising portions of the Env protein and that are likely to serve as a potent antigens in immunogenic formulations against HIV-1 infection. The present invention is directed to the N60-B1.1 antibody, bi-/tri-specific engineered antibodies, Env fusion protein immunogens, and formulations comprising the same, and methods for using the same.

Antibodies

Details regarding the discovery and characterization of the N60-B1.1 antibody are provided below. However, the antibody can be generally characterized as comprising a VK domain having the amino acid sequence set forth in SEQ ID NO:2 and a VH domain having the amino acid sequence set forth in SEQ ID NO:4, wherein the antibody exhibits binding specificity for HIV-1 Env protein. Thus, the invention is directed, in part, to an isolated antibody comprising: (a) a VK domain comprising the amino acid sequence of SEQ ID NO:2, (b) a VH domain comprising the amino acid sequence of SEQ ID NO:4, or (c) both a VK domain comprising the amino acid sequence of SEQ ID NO:2 and a VH domain comprising the amino acid sequence of SEQ ID NO:4. The antibodies are not limited with respect to other characteristics. For example, the antibodies may be of any class, such as IgG1, IgG2, IgG3, IgG4, IgM, IgA1, IgA2, IgD or IgE. The antibodies may be polyclonal, monoclonal, humanized or chimeric antibodies, and the antibodies may be in the form of an antiserum comprising the antibodies. The antibodies may be isolated antibodies, purified antibodies, exogenous antibodies, endogenous antibodies, or a combination thereof.

It will be readily understood by the skilled artisan that variations can be made to the antibodies of the present invention, for example, alterations can be made to either or both the VK and VH domains, while maintaining the binding activity and/or binding specificity of the antibody. Thus, the present invention includes variants of the antibodies defined herein that include one or more of amino acid insertions, deletions and substitutions and yet retain binding specificity for HIV-1 Env protein. In particular, the invention includes antibody variants where the VK domain has at least about 80, 81, 82, 83, 84, 85, 86, 87, 88, 89, 90, 91, 92, 93, 94, 95, 96, 97, 98, or 99% sequence identity over the entire length of the amino acid sequence set forth in SEQ ID NO:2 and the VH domain comprises the amino acid sequence of SEQ ID NO:4. The invention also includes antibody variants where the VK domain comprises the amino acid sequence of SEQ ID NO:2 and the VH domain has at least about 80, 81, 82, 83, 84, 85, 86, 87, 88, 89, 90, 91, 92, 93, 94, 95, 96, 97, 98, or 99% sequence identity over the entire length of the amino acid sequence set forth in SEQ ID NO:4. The invention further includes antibody variants where the VK domain has at least about 80, 81, 82, 83, 84, 85, 86, 87, 88, 89, 90, 91, 92, 93, 94, 95, 96, 97, 98, or 99% sequence identity over the entire length of the amino acid sequence set forth in SEQ ID NO:2 and the VH domain has at least about 80, 81, 82, 83, 84, 85, 86, 87, 88, 89, 90, 91, 92, 93, 94, 95, 96, 97, 98, or 99% sequence identity over the entire length of the amino acid sequence set forth in SEQ ID NO:4. In a non-limiting example, the invention includes an antibody variant where the VK domain has at least about 95% sequence identity over the entire length of the amino acid sequence set forth in SEQ ID NO:2 and the VH domain has at least about 95% sequence identity over the entire length of the amino acid sequence set forth in SEQ ID NO:4.

The invention also includes isolated antibodies having binding specificity for HIV-1 Env protein where the VK domain comprises amino acids 1-95 of SEQ ID NO:2 or the VH domain comprises amino acids 1-102 of SEQ ID NO:4, as well as an isolated antibody where the VK domain comprises amino acids 1-95 of SEQ ID NO:2 and the VH domain comprises amino acids 1-102 of SEQ ID NO:4.

The antibodies encompassed within the scope of the invention include fully human antibodies, humanized antibodies, as well as chimeric antibodies. The antibodies may be monoclonal or polyclonal. Further, the antibody may be a recombinant antibody.

The present invention also encompasses fragments of the antibodies defined herein that retain the ability to bind HIV-1 Env protein. The fragments included, but are not limited to, Fab fragments, F(ab')$_2$ fragments, single chain Fv (scFv) antibodies, and fragments produced by an Fab expression library, as well as bi-specific antibody and triple-specific antibodies. It will thus be clear to the skilled artisan that all references to "antibodies" herein include both full-size antibodies as well as antibody fragments, as defined herein.

The antibodies may be produced in any species of animal, though preferably from a mammal such as a human, simian, mouse, rat, rabbit, guinea pig, horse, cow, sheep, goat, pig, dog or cat. For example, the antibodies can be human antibodies or humanized antibodies, or any antibody preparation suitable for administration to a human. For the production of the antibodies, the selected species of animal can be immunized by injection with one or more antigens, e.g., the Env fusion proteins or variants discussed herein. The antigens may be administered in conjunction with one or more pharmaceutically acceptable adjuvants to increase the immunological response. Suitable adjuvants include, but are not limited to, Freund's Complete and Incomplete Adjuvant, Titermax, Oil in Water adjuvants, as well as aluminum compounds where antigens, normally peptides, are physically precipitated with hydrated insoluble salts of aluminum hydroxide or aluminum phosphate. Other adjuvants include liposome-type adjuvants comprising spheres having phospholipid bilayers that form an aqueous compartment containing the antigen and protect it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the immunogenic formulation.

Means for preparing antibodies are very well known in the art. The antibodies of the invention can be prepared using any known technique that provides for the production of antibody molecules. Suitable techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York N.Y., pp 77-96 (1985)). Each of these publications is herein incorporated by reference in its entirety. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci. USA* 86: 3833-3837 (1989), and in Winter G. and Milstein C., *Nature* 349:293-299 (1991), both of which is herein incorporated by reference in its entirety.

Humanized antibodies are those where a human antibody has been engineered to contain non-human complementarity-determining regions (CDRs) derived from an antibody produced in a non-human host against a selected antigen. Means for producing humanized antibodies are well-known in the art and include Vaswani S K, and Hamilton R G, *Ann Allergy Asthma Immunol.* 81(2):105-15 (1998) and Kashmiri S V et al., *Methods* 36 (1):25-34 (2005), each of which is herein incorporated by reference in its entirety.

Chimeric antibodies are those where an antigen binding region (e.g., F(ab')$_2$ or hypervariable region) of a non-human antibody is transferred into the framework of a human antibody by recombinant DNA techniques. Techniques developed for the production of such antibodies include the splicing of mouse antibody genes to human antibody genes to obtain a molecule with appropriate antigen specificity and biological activity. Such techniques are also well known and include: Morrison et al., *Proc Natl. Acad. Sci* 81:6851-6855 (1984); Neuberger et al., *Nature* 312:604-608(1984); Takeda et al., *Nature* 314:452-454(1985), each of which is herein incorporated by reference in its entirety.

Techniques for the production of single chain antibodies are described in U.S. Pat. No. 4,946,778, incorporated herein by reference in its entirety.

Antibody fragments such as F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse W. D. et al., Science 256:1275-1281 (1989), herein incorporated by reference in its entirety).

The bi- and tri-specific (or triple-specific) antibodies of the present invention are recombinant engineered antibodies such as those shown in FIG. 7. These antibodies can bind two (bi-specific) or three (tri-specific) different epitopes. The antigen binding domains of two or three different antibodies are combined on a constant region frame to create bi- and tri-specific antibodies. As an example, the antigen binding domains of the following antibodies can be used: (i) bnAbs against glycan-dependent V1V2 and V3 related regions, e.g., N60-B1.1, PG9 and PGT128; (ii) bnAbs against CD4bs, e.g., b12 and VRC01; (iii) ADCC antibodies against the cluster A region of gp120, e.g., JR4 and JR48.1. Similarly, the constant region of any of these antibodies can be the frame that is engineered to contain the noted antigen binding domains. Techniques for production of such antibodies are well known in the art. These antibodies may have increased potency and broader specificity in neutralizing HIV-1 than a mixture of individual Abs. For example, such antibodies may exhibit simultaneous and synergetic binding to gp120.

Antibody Formulations

The skilled artisan will understand that the antibodies and fragments thereof defined in the present invention can be used in a variety of applications, including methods of treating HIV-1 infection, methods of preventing HIV-1 infections, methods of screening agonists and antagonists of HIV-1 infection, to name only a few. Thus, the invention includes pharmaceutical formulations comprising the antibodies and/or HIV-1 Env protein binding fragments thereof and a pharmaceutically acceptable carrier (also termed antibody formulations herein). The invention also includes a kit comprising one or more of the antibodies and/or HIV-1 Env protein binding fragments thereof and instructions for using the antibodies or fragments.

The pharmaceutical formulations comprising one or more of the antibodies or fragments of the invention and a pharmaceutically acceptable carrier may be administered to a subject, such as a human, for the treatment or prevention of HIV-1 infection. Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The identity of the carrier(s) will also depend on the means used to administer pharmaceutical formulations comprising antibodies to a subject. For example, pharmaceutical formulations for intramuscular preparations can be prepared where the carrier is water-for-injection, 0.9% saline, or 5% glucose solution. Pharmaceutical formulations may also be prepared as liquid or powdered atomized dispersions for delivery by inhalation. Such dispersion typically contain carriers common for atomized or aerosolized dispersions, such as buffered saline and/or other compounds well known to those of skill in the art. The delivery of the pharmaceutical formulations via inhalation has the effect of rapidly dispersing the immunogenic formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the pharmaceutical formulations may also be administered in a liquid form. The liquid can be for oral dosage, for ophthalmic or nasal dosage as drops, or for use as an enema or douche. When the pharmaceutical formulation is formulated as a liquid, the liquid can be either a solution or a suspension of the pharmaceutical formulation. There is a variety of suitable formulations for the solution or suspension of the pharmaceutical formulations that are well known to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

Env Fusion Proteins

The invention is also directed to fusion proteins comprising a portion of the HIV-1 Env polypeptide and single-chain fragment V regions of enhancing antibodies and optionally a linker joining these two domains in a fusion protein. These Env fusion proteins include: gp120-b12-ScFV, gp120-VRC01-ScFV, gp120-JR4-ScFV and gp120-JR48.1-ScFV. Thus, the invention is directed to the gp120-b12-ScFV polypeptide comprising the amino acid sequence set forth in SEQ ID NO:8 and the polynucleotide sequence set forth in SEQ ID NO:7 which encodes the protein. The invention is also directed to the gp120-VRC01-ScFV polypeptide comprising the amino acid sequence set forth in SEQ ID NO:10 and the polynucleotide sequence set forth in SEQ ID NO:9 which encodes the protein. The invention is further directed to the gp120-JR4-ScFV polypeptide comprising the amino acid sequence set forth in SEQ ID NO:12 and the polynucleotide sequence set forth in SEQ ID NO:11 which encodes the protein. The invention is additionally directed to the gp120-JR48.1-ScFV polypeptide comprising the amino acid sequence set forth in SEQ ID NO:14 and the polynucleotide sequence set forth in SEQ ID NO:13 which encodes the protein.

The present invention is not limited to the four noted fusion proteins and variants thereof (discussed below). It encompasses all polypeptides comprising an HIV-1 Env peptide domain and a ScFV domain of an enhancing antibody, and an optional linker peptide domain for connecting these domains. The HIV-1 Env peptide domain will generally encompass amino acids of gp120 (amino acids 1-509 of SEQ ID NO:14) and gp140 (amino acids 1-693 of SEQ ID NO:14) of the HIV-1 Env polypeptide. The linker domain may be a GSA linker [27], such as GSSGGGGSGSGGGGSGGGAAA (SEQ ID NO:15) as a non-limiting example. Acceptable enhancing antibodies include, but are not limited to, CD4bs bnAbs (e.g., b12 [16], VRC01 [7]) as well as cluster A ADCC mAbs (e.g., JR4, JR48.1 [28]). The ScFV domain generally comprises a heavy chain variable domain and a light chain variable domain with a 15 amino acid GS linker (GGGGSGGGGSGGGGS; SEQ ID NO:16).

As with the antibodies above, the invention is also directed to variants of gp120-b12-ScFV, gp120-VRC01-ScFV, gp120-JR4-ScFV and gp120-JR48.1-ScFV. The skilled artisan will readily appreciate that minor changes can be made to the fusion protein without altering the ability of the proteins to induce an immune response. Thus, the invention includes variants of the fusion proteins defined herein that include one or more of amino acid insertions, deletions and substitutions. In particular, the invention includes fusion protein variants having at least about 80, 81, 82, 83, 84, 85, 86, 87, 88, 89, 90, 91, 92, 93, 94, 95, 96, 97, 98, or 99% sequence identity over the entire length with one of the four fusion proteins defined herein (i.e., gp120-b12-ScFV, gp120-VRC01-ScFV, gp120-JR4-ScFV and gp120-JR48.1-ScFV).

The invention also encompasses variants having about 80% or greater sequence identity within only one or two of the domains of the gp120-b12-ScFV, gp120-VRC01-ScFV, gp120-JR4-ScFV and gp120-JR48.1-ScFV polypeptides. For example, the amino acid changes may be limited to one or more of: (i) the HIV-1 Env peptide domain of the polypeptide, (ii) the linker domain of the polypeptide, and (iii) the ScFV domain of the polypeptide. The skilled artisan will appreciate that the linker domain is an especially suitable location for amino acid changes as changes therein would be expected to have very minor effects on ability of the polypeptide to induce particular immune responses in a subject. As with the changes over the entire length of the polypeptide discussed above, variants of the individual domains include those having at least about 80, 81, 82, 83, 84, 85, 86, 87, 88, 89, 90, 91, 92, 93, 94, 95, 96, 97, 98, or 99% sequence identity over the entire length of a particular domain.

Fusion Protein Formulations

The Env fusion proteins and variants of the invention can be used to induce an immune response in a subject, such as a human. When the subject is a non-human animal, antibodies can be collected after immunization, processed appropriately, and then used in methods of treatment or prevention in humans. Alternatively, Env fusion proteins and variants of the invention can be administered directly to a human subject or non-human subject to induce endogenous production of therapeutic or protective HIV-1 binding antibodies. The Env fusion proteins and variants can therefore be used in the treatment of a subject suffering from or susceptible to HIV-1 infection. In most instances, the Env fusion proteins and variants will be prepared in an immunogenic formulation comprising one or more of the Env fusion proteins or variants and a pharmaceutically acceptable carrier and/or adjuvant. In a non-limiting example, an immunogenic formulation of the invention comprises: (a) one, two, three or all four of the polypeptides gp120-b12-ScFV (SEQ ID NO:8), gp120-VRC01-ScFV (SEQ ID NO:10), gp120-JR4-ScFV (SEQ ID NO:12) and gp120-JR48.1-ScFV (SEQ ID NO:14) and a pharmaceutically acceptable carrier and/or adjuvant, or (b) the formulation of (a) wherein at least one of the polypeptides is a variant and wherein the variant has at least about 95% sequence identity with the full length reference sequence. In an exemplary, but not limiting aspect, the invention is directed to an immunogenic formulation comprising each of the polypeptides gp120-b12-ScFV (SEQ ID NO:8), gp120-VRC01-ScFV (SEQ ID NO:10), gp120-JR4-ScFV (SEQ ID NO:12) and gp120-JR48.1-ScFV (SEQ ID NO:14) and a pharmaceutically acceptable carrier and/or adjuvant. Pharmaceutically acceptable carriers and adjuvants are as described above.

Vectors

As discussed above, the Env fusion proteins and variants that are used to induce production of anti-HIV-1 antibodies can be administered directly to a subject, either "naked" or in the context of an immunogenic formulation. In addition, expression vectors encoding the Env fusion proteins and variants may be administered to the subject, whereupon the encoded fusion proteins and variants are produced, which in turn act as immunogens to induce production of anti-HIV-1 antibodies.

Thus, the invention also provides expression vectors encoding one or more of the Env fusion proteins of SEQ ID NOs:8, 10, 12 and 14 and/or one or more Env fusion protein variants. A particular vector can encode one or more than one of the fusion proteins and variants. When a single expression vector encodes more than one fusion protein or variant, the coding regions are arranged in 5' to 3' alignment on the vector with suitable spacing between the different coding regions.

The invention further provides pharmaceutical formulations comprising one or more of the vectors and a pharmaceutically acceptable carrier. In one aspect the invention provides pharmaceutical formulations comprising expression vectors encoding 1, 2, 3 or 4 of the fusion proteins and a pharmaceutically acceptable carrier. Other exemplary formulations include, but are not limited to, formulations comprising expression vectors encoding 1, 2, 3, 4 or more variants.

The skilled artisan will understand that there is a wide variety of expression vector combinations that may make up the pharmaceutical formulations. For example, a pharmaceutical formulation may be prepared where all of the expression vectors therein have the same nucleotide sequence. As an illustration, the vector may encode only one of the fusion proteins of SEQ ID NOs:8, 10, 12 and 14, or the same vector may encode two, three or all four of the fusion proteins, arranged in 5' to 3' alignment on the vector with suitable spacing between the different coding regions. Alternatively, a pharmaceutical formulation may be prepared comprise expression vectors of two or more different sequences. Pharmaceutically acceptable carriers are as described above.

As will be described in detail below, the vectors and pharmaceutical formulations comprising the vectors can be used to induce HIV-1 antibody production in a subject, which in turn can be used in methods of treatment or prevention in the subject. The vectors and pharmaceutical formulations can therefore be used in the treatment of a subject suffering from or susceptible to HIV-1 infection.

Methods of Using Antibodies

The pharmaceutical formulations comprising the antibodies and/or HIV-1 Env protein binding fragments thereof can be used in a variety of applications. Such applications include, but are not limited to, passive immunization which results in the treatment or prevention of HIV-1 infection in a subject. Thus, the invention is directed to a method of treating an HIV-1 infection in a subject, comprising administering a therapeutically effective amount of a pharmaceutical formulation as defined herein to a subject having an HIV-1 infection, thereby treating an HIV-1 infection in a subject. In a related aspect, the invention includes methods of preventing an HIV-1 infection in a subject, comprising administering a therapeutically effective amount of a pharmaceutical formulation as defined herein to a subject at risk of developing an HIV-1 infection, thereby inhibiting an HIV-1 infection in a subject.

As used herein, the terms "treat", "treating" and "treatment" have their ordinary and customary meanings, and include one or more of, ameliorating a symptom of HIV-1 infection, blocking or ameliorating a recurrence of a symptom of HIV-1 infection, decreasing in severity and/or frequency a symptom of HIV-1 infection. Treatment means ameliorating, blocking, reducing, decreasing or inhibiting by about 1% to about 100% versus a subject to which the treatment has not been administered. Preferably, the ameliorating, blocking, reducing, decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of the infection. Thus, the subject may be infected with HIV-1 or merely be susceptible to the infection. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "prevent", "preventing" and "prevention" have their ordinary and customary meanings, and include one or more of, stopping, averting, avoiding, alleviating or blocking the occurrence of a symptom of HIV-1 infection, the recurrence of a symptom of HIV-1 infection, the development of HIV-1 infection or the progression of HIV-1 infection. Prevention means stopping by at least about 95% versus a subject to which the prevention has not been administered. Preferably, the stopping is about 100%, about 99%, about 98%, about 97%, about 96% or about 95%. The course of therapy may begin prior to, concurrent with, or after the onset of clinical symptoms of the infection. Thus, the subject may be infected with HIV-1 or merely be susceptible to the infection. The results of the prevention may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

In each of the methods of treatment and prevention of the present invention the pharmaceutical formulations comprising the antibodies and/or HIV-1 Env protein binding fragments are administered in a pharmaceutically acceptable form and in substantially non-toxic quantities. These pharmaceutical formulations may be administered to a subject using different schedules, depending on the particular disease being treated or prevented, and severity thereof; the age and size of the subject; and the general health of the subject, to name only a few factors to be considered. In general, the pharmaceutical formulations may be administered once, or twice, three times, four times, five times, six times or more, over a course of treatment or prevention. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of protein in the formulation may be administered in each dose of the dosing schedule, or the amounts in each dose may vary. The identity of the particular antibodies and variants in the formulation may also vary or remain the same in each dose in a dosing schedule.

The amount of the antibody and/or variant administered to a subject in a dose when the methods of the present invention are practiced will again vary. However, the amount administered to a subject in a dose will be sufficient to effect treatment or prevention of HIV-1 infection in a subject. As an example, a therapeutically effective amount of antibody and/or variant in a dose of a pharmaceutical formulation of the present invention is typically between about 10 to about 200 mg per kg of body weight of the subject to which the dose of the pharmaceutical formulation is be administered.

Appropriate doses and dosing schedules can readily be determined by techniques well known to those of ordinary skill in the art without undue experimentation. Such a determination will be based, in part, on the tolerability and efficacy of a particular dose.

Administration of the pharmaceutical formulations may be via any of the means commonly known in the art of vaccine delivery. Such routes include intravenous, intraperitoneal, intramuscular, subcutaneous and intradermal routes of administration, as well as nasal application, by inhalation, ophthalmically, orally, rectally, vaginally, or by any other mode that results in the formulation contacting mucosal tissues.

Methods of Using Env Fusion Proteins

The invention provides methods of using the Env fusion proteins as immunogens to generate an immune response in a subject (active immunization). The methods comprise administering one or more of the Env fusion proteins, and/or one or more of the variants thereof, typically as an immunogenic formulation, to a subject in which it is desired that an immune response be generated. The Env fusion proteins and variants may be administered to the subject in the form of the vectors as defined above, or pharmaceutical compositions comprising the vectors. The Env fusion proteins and variants may also be administered to the subject in the form of the proteins themselves, whether alone or in an immunogenic formulation comprising the protein/variants and a pharmaceutically acceptable carrier and/or adjuvant.

Exemplary immunogenic formulations include, but are not limited to, formulations comprising SEQ ID NO:8, SEQ ID NO:10, SEQ ID NO:12, SEQ ID NO:14, SEQ ID NOs:8 and 10, SEQ ID NOs:10 and 12, SEQ ID NOs:12 and 14, SEQ ID NOs:8 and 14, SEQ ID NOs:8, 10 and 12, SEQ ID NOs:10, 12 and 14, SEQ ID NOs:8, 10 and 14, SEQ ID NOs:8, 12 and 14, or SEQ ID NOs:8, 10, 12 and 14.

In a non-limiting example, the invention is directed to a method of generating an immune response in a subject comprising administering an immunologically effective amount of an immunogenic formulation as defined herein to a subject, thereby generating an immune response in a subject. In a related aspect, the invention is directed to a method of generating a protective immune response in a subject comprising administering an immunologically effective amount of an immunogenic formulation as defined herein to a subject, thereby generating a protective immune response in a subject. Other exemplary formulations include, but are not limited to, formulations comprising 1, 2, 3, 4 or more variants.

In each of the methods of active immunization, the immunogenic formulations comprising the fusion proteins, variants and/or vectors are administered in a pharmaceutically acceptable form and in substantially non-toxic quantities. The immunogenic formulations may be administered to a subject using different schedules, depending on, for example, the contents of the immunogenic formulation; the age and size of the subject; and the general health of the subject, to name only a few factors to be considered. In general, the immunogenic formulations may be administered once, or boosted twice, three times, four times, five times, six times or more, over a course of immunization. The timing between each booster may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of protein in the formulation may be administered in each dose, or the amounts in each dose may vary. The identity of the particular fusion proteins, variants and vectors in the formulation may also vary or remain the same in each dose.

The amount of the fusion proteins, variants and vectors administered to a subject in a dose when immunization is practiced will vary. However, the amount administered to a subject in a dose will be sufficient to induce an immune response in the subject. As an example, a immunologically effective amount of fusion proteins, variants and/or vectors in a dose of an immunogenic formulation of the present invention is typically between about 10 to about 500 ug of protein.

Appropriate doses and booster schedules can readily be determined by techniques well known to those of ordinary skill in the art without undue experimentation. Such a determination will be based, in part, on the tolerability and efficacy of a particular dose.

Administration of the immunogenic formulations may be via any of the means commonly known in the art of vaccine delivery. Such routes include intravenous, intraperitoneal, intramuscular, subcutaneous and intradermal routes of administration, as well as nasal application, by inhalation, ophthalmically, orally, rectally, vaginally, or by any other mode that results in the formulation contacting mucosal tissues.

The term "subject" is intended to mean an animal, such birds or mammals, including humans and animals of veterinary or agricultural importance, such as dogs, cats, horses, sheep, goats, and cattle.

A kit comprising the necessary components for active immunization, including a immunogenic formulation comprising one or more fusion proteins or variants thereof that elicits an immune response and instructions for its use, is also within the purview of the present invention. In addition, a kit comprising the necessary components for passive immunization, including a pharmaceutical formulation comprising one or more antibodies or variants thereof with binding specificity for HIV-1 Env and instructions for its use, is within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

EXAMPLES

N60-B1.1 Antibody

A novel HIV-1 broadly neutralizing human antibody (bnAb) was cloned and termed N60-B1.1. The antibody was identified by neutralization screening of limiting dilution B cell cultures from a local volunteer NVS60 who has an ongoing broadly neutralizing antibody response and a low but detectable HIV-1 viral load of approximately 100 copies/ml [21, 22]. Limiting dilution B cell cultures were performed as previously described [22] and the neutralization assay was based on the standard TZM-b1 assay. N60-B1.1 neutralized 40% of a panel of 118 tier 2,3 viruses with an average IC50 of 0.44 ug/ml (Table 1). The neutralization pattern of N60-B1.1 is complementary to other bnAbs in that it potently neutralizes some viruses that are more resistant to other bnAbs (e.g., VRC01, VRCPG04) as shown in Table 2. This demonstrates the unique aspects of N60-B1.1 as a novel type of HIV-1 bnAb.

TABLE 1

Potency and breath of neutralization activity of N60-B1.1

|  | N60-B1.1 | N60-B1.2 | 3BNC117 | 3BNC55 | 45-46 | 12A12 | 8ANC195 | VRC01 | VRCPG04 | PG9 | PG16 | b12 |
| --- | --- | --- | --- | --- | --- | --- | --- | --- | --- | --- | --- | --- |
| # of tested viruses | 122 | 110 | 119 | 119 | 119 | 119 | 119 | 85 | 55 | 73 | 73 | 120 |
| Median IC50 (ug/ml) | 0.37 | 1.51 | 0.09 | 0.55 | 0.07 | 0.22 | 0.87 | 0.21 | 0.18 | 0.10 | 0.03 | 3.20 |
| % of neutralized viruses | 40.2 | 21.8 | 89.1 | 65.5 | 89.1 | 94.1 | 66.4 | 88.2 | 72.7 | 83.6 | 84.9 | 38.3 |

TABLE 2

Unique neutralization pattern of N60-B1.1

| | | IC50 Titer (ug/ml) of antibodies | | | | | |
| --- | --- | --- | --- | --- | --- | --- | --- |
| Virus ID | Clade* | N60-B1.1 | N60-B1.2 | 3BNC117 | 3BNC55 | 45-46 | 12A12 |
| SF162.LS | B-1A | $0.019^d$ | $0.07^d$ | NT | NT | NT | NT |
| BaL.26 | B-1B | $0.019^d$ | $0.04^d$ | $0.090^d$ | >30 | $0.040^d$ | $0.017^d$ |
| 6535.3 | B | $0.019^d$ | $0.019^d$ | $0.550^b$ | $2.600^b$ | $0.140^c$ | $21.970^a$ |
| AC10.0.29 | B | $0.14^c$ | $0.94^c$ | $13.840^a$ | >50 | $0.420^c$ | $1.150^b$ |
| THRO4156.18 | B | $0.30^c$ | $30.71^a$ | $1.760^b$ | >50 | $1.590^b$ | $3.050^b$ |
| CAAN5342.A2 | B | $0.019^d$ | $0.25^c$ | $0.420^c$ | $4.100^b$ | $0.110^c$ | $1.320^b$ |
| 1006_11_C3_1601 | B (T/F) | $0.07^d$ | $1.25^b$ | $0.030^d$ | >50 | $0.050^d$ | $0.220^c$ |
| ZM53M.PB12 | C | $0.019^d$ | $0.38^c$ | $0.210^c$ | $12.550^a$ | $0.190^c$ | $0.590^c$ |
| Du172.17 | C | $7.08^b$ | >50 | $1.190^b$ | $3.520^b$ | >30 | $0.200^c$ |
| Du422.1 | C | $0.18^c$ | $1.71^b$ | >50 | >50 | >50 | >50 |
| T250-4 | CRF02_AG | $0.019^d$ | $0.019^d$ | >15 | $0.240^c$ | >30 | >30 |
| 3817.v2.c59 | CD | $1.53^b$ | NT | $0.150^c$ | >50 | >50 | $23.740^a$ |
| 6540.v4.c1 | AC | $0.08^d$ | $2.16^b$ | >50 | >50 | >50 | $0.110^c$ |
| 6545.v4.c1 | AC | $0.37^c$ | NT | >50 | >50 | >50 | $0.250^c$ |

| | | IC50 Titer (ug/ml) of antibodies | | | | | |
| --- | --- | --- | --- | --- | --- | --- | --- |
| | Virus ID | 8ANC195 | VRC01 | VRC-PG04 | PG9 | PG16 | b12 |
| | SF162.LS | NT | $0.237^c$ | $0.088^d$ | >50 | >50 | NT |
| | BaL.26 | >50 | $0.100^d$ | $0.503^c$ | $0.034^d$ | $0.136^c$ | $0.200^c$ |

TABLE 2-continued

| Unique neutralization pattern of N60-B1.1 | | | | | | |
|---|---|---|---|---|---|---|
| 6535.3 | 0.200$^c$ | 0.540$^c$ | 0.840$^c$ | 0.465$^c$ | >50 | 17.5$^a$ |
| AC10.0.29 | 0.880$^c$ | 2.200$^b$ | >50 | 0.078$^d$ | 0.02$^d$ | 1.9$^b$ |
| THRO4156.18 | >50 | 2.300$^b$ | >50 | 15.000$^a$ | 0.975$^c$ | 0.5$^c$ |
| CAAN5342.A2 | >50 | 0.820$^c$ | 1.660$^b$ | 13.000$^a$ | 7.430$^b$ | >50 |
| 1006_11_C3_1601 | 0.430$^c$ | 0.150$^c$ | NT | 0.366$^c$ | >50 | 3.9$^b$ |
| ZM53M.PB12 | 9.630$^b$ | 1.300$^b$ | 4.280$^b$ | 0.092$^d$ | 0.009$^d$ | 25.9$^a$ |
| Du172.17 | 10.800$^a$ | >50 | 0.218$^c$ | 0.262$^c$ | 0.030$^d$ | 1$^c$ |
| Du422.1 | >50 | >50 | >50 | 0.303$^c$ | 0.02$^d$ | 0.2$^c$ |
| T250-4 | >50 | >50 | >50 | 0.001$^d$ | 0.001$^d$ | >50 |
| 3817.v2.c59 | 1.000$^c$ | >50 | 3.760$^b$ | 0.007$^d$ | 0.006$^d$ | >50 |
| 6540.v4.c1 | >50 | >50 | >50 | 0.035$^d$ | 0.017$^d$ | 46.1$^a$ |
| 6545.v4.c1 | 26.940$^a$ | >50 | >50 | 0.095$^d$ | 0.068$^d$ | >50 |

Code(<):
50.00$^a$
10.00$^b$
1.00$^c$
0.10$^d$
*(T/F): Transmitted/Founder Virus
NT: Not tested The amino acid sequences of the variable regions of N60-B1.1 are shown in FIG. 1, along with the light chain variable region (VK) of the clone N60-B1.2 (the un-mutated germline VK gene) and the heavy chain variable region (VH) of the un-mutated germline VH gene IGHV4-39*01. The VK and VH sequences were determined by IMGT/V-QUEST (see the website having the url beginning with "www" and ending with "imgt.org/IMGT_vquest/vquest") sequence analysis. Further, the DNA and amino acid sequences of the VK chain of N60-B1.1 are provided in SEQ ID NOs:1 and 2, respectively, while the DNA and amino acid sequences of the VH chain of N60-B1.1 are provided in SEQ ID NOs:3 and 4, respectively.

N60-B1.1 is encoded by VH4-39*07 that is somatically mutated 13.3% at the nucleotide level and 24.5% at the amino acid level, which is within the normal somatic mutation rate of an antibody response in vivo. It uses a single point mutated light chain of germline (CDRL3) VK3-15*01. This is distinct from other bnAbs, which have exceptionally high rates of somatic mutation in this chain. Therefore, the induction of an Ab response of N60-B1.1-like antibodies should not be limited by the bottle-neck of somatic mutation that is required for other bnAbs against HIV-1.

N60-B1.1 binds to monomeric gp120 with low affinity and the binding was detectable most reproducibly by ELISA [22]. The antibody binds to intact virions as evidenced by fluorescence correlation spectroscopy and binds cell surface expressed gp160 as detected by flow cytometry. The antibody also binds virions attached to target cells with biphasic kinetics as showed by time course immunofluorescence confocal microscopy.

Mutagenesis studies indicate that N60-B1.1 binds a novel epitope in gp120 that is different from other reported bnAbs. As shown in FIG. 2, mutations in the V1/V2 loop (dV1V2), the co-receptor binding site (CoRbs, I420R), and the V3 loop (dV3) affect N60-B1.1 binding to monomeric gp120. It does not bind to linear peptides of Env. Its binding to gp120 can be modulated by CD4 interaction with gp120 (FLSC) but the epitope is not affected by mutation (D368R) that abrogate CD4 binding site epitopes. In early studies, it was established that N60-B1.1 does not bind to linear Env peptides. Further, it was found that N60-B1.1 binds to monomeric BaL gp120 with low avidity and its binding is detectable most reproducibly by capture ELISA [22].

To map the epitope of N60-B1.1, its binding to a large panel of gp120 mutants was tested by capture ELISA [22]. As shown in Table 3, mutants affecting the co-receptor binding site (CoRbs, I420R, I423A), deletion of the V1/V2 loop (dV1V2) and deletion of the V3 loop (dV3) and a minimal V3 loop mutant (mV3) [23] all abrogate N60-B1.1 binding to monomeric gp120.

TABLE 3

| | Mapping N60-B1.1 in gp120 mutants | | | | | |
|---|---|---|---|---|---|---|
| | % Binding | N60-B1.1 | 17b | b12 | 2G12 | N12-O3.1 |
| Wild-type | BaL-gp120 | 100 | 100 | 100 | 100 | 100 |
| N-terminal | -E31A | 103 | 100 | 86 | 80 | 100 |
| Extension | -E32A | 108 | 113 | 104 | 93 | 100 |
| | -K33A | 76 | 48$^d$ | 89 | 83 | 100 |
| | -W35A | 132$^c$ | 140$^c$ | 107 | 99 | 100 |
| | -Y39A | 121 | 113 | 90 | 89 | 100 |
| | -Y40A | 139$^c$ | 143$^c$ | 106 | 93 | 100 |
| Beta-Sandwich 1 | -V44A | 114 | 105 | 94 | 93 | 100 |
| | -W45A | 84 | 37$^d$ | 96 | 92 | 100 |
| | -K46A | 50$^d$ | 26$^d$ | 93 | 92 | 100 |
| | -E47A | 78 | 26$^d$ | 100 | 96 | 100 |
| | -E47AE91A | 73$^d$ | 11$^a$ | 86 | 86 | 100 |
| Layer 1 | -F53A | 90 | 48$^d$ | 91 | 99 | 100 |
| | -D57A | 98 | 85 | 95 | 91 | 100 |
| | -D57AD62A | 76 | 48$^d$ | 103 | 105 | 100 |
| | -D57AD78A | 103 | 74$^d$ | 96 | 95 | 100 |
| | -R58AK59A | 92 | 76 | 101 | 88 | 100 |
| | -Y61A | 92 | 87 | 85 | 81 | 100 |
| | -D62A | 80 | 49$^d$ | 98 | 86 | 100 |
| | -V68A | 68$^d$ | 53$^d$ | 83 | 82 | 100 |
| | -W69A | 84 | 30$^d$ | 97 | 87 | 100 |
| | -V75A | 104 | 64$^d$ | 93 | 89 | 100 |
| | -P76A | 102 | 76 | 96 | 90 | 100 |
| | -D78A | 108 | 74$^d$ | 92 | 87 | 100 |
| Layer 2 | -H105A | 88 | 85 | 100 | 89 | 100 |
| | -E106AD107A | 36$^d$ | 6$^a$ | 80 | 79 | 100 |
| Outer Domain | -D368R | 99 | 117 | 0$^b$ | 82 | 100 |
| | -I420R | 22$^a$ | 0$^b$ | 101 | 93 | 100 |
| | -I423A | 0$^b$ | 0$^b$ | 96 | 94 | 100 |
| | -T455A | 73$^d$ | 93 | 90 | 87 | 100 |
| Layer 3 | -R476A | 57$^d$ | 20$^a$ | 101 | 98 | 100 |
| | -R476AR480A | 5$^b$ | 0$^b$ | 68$^d$ | 83 | 100 |
| | -K487AK490A | 31$^d$ | 5$^a$ | 85 | 83 | 100 |
| Beta-Sandwich 3 | -I491A | 85 | 47$^d$ | 98 | 92 | 100 |
| | -E492A | 113 | 96 | 105 | 93 | 100 |
| | -P493A | 92 | 70$^d$ | 95 | 93 | 100 |
| C-terminal Extension | -L494A | 99 | 96 | 95 | 79 | 100 |
| | -G495A | 106 | 106 | 90 | 93 | 100 |
| | -V496A | 107 | 114 | 100 | 96 | 100 |
| | -p498A | 101 | 100 | 97 | 93 | 100 |
| | -T499A | 102 | 81 | 107 | 100 | 100 |
| | -K500A | 94 | 100 | 93 | 92 | 100 |

TABLE 3-continued

Mapping N60-B1.1 in gp120 mutants

| | % Binding | N60-B1.1 | 17b | b12 | 2G12 | N12-O3.1 |
|---|---|---|---|---|---|---|
| Variable | -dV1 | $0^b$ | $134^c$ | 90 | 93 | 100 |
| Loop | -dV2 | $0^b$ | $174^c$ | 87 | 82 | 100 |
| Deletions | -dV3 | $0^b$ | $0^b$ | 109 | 100 | $0^b$ |
| N/C- | -mV3 | $0^b$ | 85 | 100 | 100 | $0^b$ |
| terminal | core-D7 | $0^b$ | $0^b$ | 106 | 100 | $0^b$ |
| Deletions | core-V1V2-D7 | 0 | 013 | 103 | 100 | $0^b$ |
| | core-V3-D7 | $0^b$ | $285^c$ | 102 | 86 | 100 |
| Glycan | S158A | $3^b$ | $62^d$ | 80 | 80 | 100 |
| mutant | T162A | 100 | 101 | 110 | 87 | 100 |
| | S200A | $22^a$ | $55^d$ | 86 | 92 | 100 |
| | T303A | $2^b$ | 100 | 92 | 88 | 100 |
| | S334A | 91 | 95 | $nd^e$ | $16^a$ | 100 |
| sCD4 complex | FLSC | $10^a$ | $266^e$ | $24^a$ | 104 | 100 |

Scale
$<75^d$
$<25^a$
$<5^b$
$>125^e$
0: OD = background

N60-B1.1 is a glycan-dependent bnAb as the removal of selected glycosylation sites at V1V2 region (S158A and S200A) and V3 region (T303A) substantially decrease its binding abilities. Removal of N160 and N332 glycosylation sites do not affect its binding, which indicates that N60-B1.1 is different from other reported glycan-dependent PG9-like and PGT series bnAbs. Interestingly, N60-B1.1 binding to gp120 is decreased on gp120-CD4 complexes as evidenced by the substantially decreased binding to gp120-sCD4 fusion protein FLSC. In addition, the N60-B1.1 epitope is not affected by mutation (D368R) that abrogates CD4bs epitopes. Collectively, these results indicate that N60-B1.1 binds a glycan dependent co-receptor associated epitope involving the V1V2 and V3 region, which is different from that of other reported bnAbs, such as PG9, PG16, PGT128 and VRC01. N60-B1.1 is not a traditional CD4i or CD4bs mAb because it does not bind well to FLSC or BaL-gp120-I420R mutants, but binds well to a BaL-gp120-D368R mutant. It is not a PG9-like bnAb because N60-B1.1 binds reasonably well to monomeric gp120 and shows a different neutralization profile from that of PG9 (for example, it potently neutralizes the PG9 resistant SF162 virus).

Importantly, N60-B1.1 is a protective bnAb without auto-reactivity as shown in FIG. 3A. Most reported HIV-1 bnAbs showed auto/poly-reactivity [7, 8, 10]. Further, there is evidence that auto-reactivity can delete "2F4 and 4E10 like" anti-gp41 B cell response in vivo [12, 24, 25]. For this reason, the auto-reactivity of N60-B1.1 was tested. As shown in FIG. 3A, N60-B1.1 is not auto-reactive, in contrast to the well-studied bnAbs of 4E10 and 2F5. N60-B1.1 is also not as poly-reactive as PG9. It should be noted that while the thresholds of detrimental auto/poly-reactivity for B cell responses in vivo is not yet well-defined, it is well known that high affinitive auto-reactive and ploy-reactive B cells are negatively selected during B cell development and the germinal center reaction [12, 24, 25]. Therefore, it is unlikely that N60-B1.1-like bnAb responses will be impacted by clonal deletion or anergy during B cell development.

To determine whether N60-B1.1 can provide protection in vivo, passive immunization studies were performed in rhesus macaque/SHIV162p3 models. As shown in FIG. 3B, in screening study, a single injection of N60-B1.1 could transiently reduce viral loads by 2 logs in SHIV162p3 infected rhesus macaques. This result indicates that N60-B1.1 is a potential protective bnAb. To test if N60-B1.1 can afford sterilizing immunity, passive immunization was performed in naive rhesus macaques. After establishing mAb decay in vivo in a PK study, eight macaques per experimental group were intravenously-infused with N60-B1.1 at 25 mg/kg body weight eight hours before an intra-rectal challenge with a SHIV162P3 stock at a 1:100 dilution. This challenge dose was previously determined to infect approximately 100% of the rhesus macaques used for in vivo titration. Monoclonal antibody b12 was used as a positive control for protection. As shown in FIG. 3C, the infusion of N60-B1.1 afforded statistically significant sterilizing immunity against the intra-rectal challenge of SHIV162P3. This is thought to be the first study showing that a bnAb can passively protect against a rectal challenge of this hard-to-neutralize virus. It should be noted that the challenge dose is slightly greater than the in vivo infection curve from the titration study. So it is not surprising that one animal out of the 8 animals of the control group remained uninfected. These studies demonstrated that N60-B1.1 is a novel protective bnAb and support the use N60-B1.1 as template for HIV-1 vaccine design.

Collectively, these data show that N60-B1.1 recognizes a novel epitope, the co-receptor associated region (CAR) of Env that involves V1/V2 and V3 regions, and is distinct from the other known bnAbs, such as PG9, PG16, PGT128 and VRC01.

Env Fusion Proteins

Characterization of N60-B1.1 binding to antigen revealed that it could define a common transitional conformation structure of HIV-1 Env. Competition ELISA was performed with a 50% binding dose of biotin-labeled N60-B1.1 together with a serial diluted amount of competing antibody in above capture ELISA. The result showed that the N60-B1.1 binding to gp120 was competed by V1V2 mAbs 2158 and 697-20D, V3 mAbs (N10-O2.1, N12-O3.1) and traditional CD4i mAb (17b, N60-i1.1) that binds CoRBS (FIG. 4A). This is consistent to the above mutagenesis studies that showed N60-B1.1 recognizes a novel co-receptor associated region (CAR) that involves V1/V2 and V3 regions.

Interestingly, binding of N60-B1.1 to gp120 was inhibited by non-broadly neutralizing CD4bs mAbs (b13, F105, N12-B2), while broadly neutralizing CD4bs mAbs, like b12 and VRC01, do not compete N60-B1.1 binding to gp120 (FIG. 4B). Instead, b12 and VRC01 substantially enhance N60-B1.1 binding to gp120, as shown in FIG. 4B. This unique feature of N60-B1.1 that could differentiate non-broadly neutralizing CD4bs mAbs (b13, F105, N12-B2, etc.) from broadly neutralizing CD4bs mAbs (b12, VRC01), therefore, defines a common transitional conformation structure of gp120, to which both bnAbs of CD4bs and N60-B1.1 can bind simultaneously. Remarkably, this observation also indicated that the common transitional conformation structure of gp120 can be stabilized by bnAb against gp120, like b12, VRC01, as well as non-neutralizing ADCC functional Abs against conserved regions of HIV-1 Env, like JR4, C11, JR48.1 (FIG. 4C), because of the enhanced binding of N60-B1.1 to complex of gp120 with these mAbs.

Non-broadly neutralizing CD4bs mAbs compete the binding of N60-B1.1 to gp120. In contrast, broadly neutralizing CD4bs mAbs enhance the binding of N60-B1.1 to gp120. This observation also indicates that bnAbs against HIV-1 gp120 may share a common neutralizing mechanism in that they neutralize HIV-1 by locking the Env trimers on virion in a transitional conformation structure, which N60-B1.1 and VRC01 can bind to, that is unable to proceed to the fusion step of HIV-1 infection.

Notably, these competitive mAbs of V1V3, V3, CD4i and CD4bs do not block neutralizing activity of N60-B1.1. Therefore, characterization of N60-B1.1 defined a common transitional conformation structure of Env that is a novel target for HIV-1 bnAbs and HIV-1 vaccine.

This observation that selected mAbs enhance the binding of N60-B1.1 to gp120 led to the design of vaccine immunogens that preferentially expose the epitope of the bnAb N60-B1.1 and that can potentially induce bnAb responses similar to that which resulted in N60-B1.1.

The following immunogen design strategy was followed. Recombinant fusion protein constructs of Env linked to single-chain fragment V region (ScFV) of enhancing mAbs were designed that can expose the binding site of N60-B1.1. These Env-ScFV proteins (for example: gp120-b12-ScFV (SEQ ID NO:8), gp120-VRC01-ScFV (SEQ ID NO:10), gp120-JR4-ScFv (SEQ ID NO:12) and gp120-JR48.1-ScFV (SEQ ID NO:14) substantially expose the epitopes of N60-B1.1 as proved by ELISA. As shown in FIG. 5, fusion protein of gp120-b12-ScFv and gp120-VRC01-ScFv enhanced the exposure of epitope of bnAb N60-B1.1 compared with that of wild type gp120 protein. Notably, they also enhanced the exposure of epitopes of other bnAbs PG9 and PGT128. These observations highlight the potential value of this type of fusion protein as a vaccine candidate for inducing bnAb response against HIV-1. They also further support the above observation that bnAbs against HIV-1 gp120 may share a common neutralizing mechanism. They neutralize HIV-1 by locking the Env trimers on virion in a common inactive transitional conformation structure that different types of bnAbs against gp120, N60-B1.1, VRC01, PG9 and PGT128, etc., can simultaneously bind to.

gp120-ScFv fusion proteins were designed for the four mAbs that enhance the exposure of the N60-B1.1 epitope on gp120. As predicted (FIG. 5), these gp120-ScFV proteins (gp120-b12-ScFV, gp120-VRC01-ScFV, gp120-JR4-ScFv and gp120-JR48.1-ScFV) stably expose the epitope recognized by N60-B1.1 as compared with the wild type gp120 protein. Further, they also enhanced the exposure of epitopes recognized by other bnAbs, like PG9 and PGT128 (FIG. 6 and Table 4).

This contrasts with the gp120-sCD4 (FLSC) protein [26, 27] to which these bnAbs bind poorly. In addition, the fusion proteins also enhance the exposure of epitopes recognized by potent ADCC mAbs that were described previously [28]. Similar to FLSC, the new type of fusion protein of gp120 with ScFV of enhancing mAbs, can substantially expose the epitopes recognized by traditional co-receptor binding site (CoRbs) CD4i Abs (N12-i2), with the exception of gp120-b12-ScFV, as summarized in Table 4. The gp120-b12-ScFv stands unique in this regard in that it blocks the exposure of epitopes recognized by traditional CD4i mAbs (N12-i2). Interestingly, these four gp120-ScFV fusion proteins are different in the exposure of epitopes recognized by cluster A ADCC mAbs. The fusion proteins gp120-b12-ScFV and gp120-VRC01-ScFV can substantially expose the epitopes recognized by all three subgroups of cluster A ADCC mAbs [28]: A32 like Abs (N5-i5), C11 like Abs (N12-i3) and Abs competing with both A32 and C11 (JR4) (Table 4). By contrast, the fusion protein gp120-JR4-ScFv is not recognized by any cluster A ADCC mAbs, whereas the gp120-JR48.1-ScFv fusion protein exposes the epitopes recognized by A32-like antibodies (N5-i5) and antibodies competing with both A32 and C11 (JR4), but inhibits epitopes of C11-like Abs (N12-i3). As expected, the fusion proteins of gp120-b12-ScFV and gp120-VRC01-ScFV do not bind CD4bs bnAbs (Table 4) as compared with gp120. On the other hand, the gp120-JR4-ScFV and gp120-JR48.1-ScFV fusion proteins stably express the epitopes recognized by CD4bs bnAbs (b12, VRC01 and PG04).

In addition, these fusion proteins enhance the exposure of epitopes for potent ADCC mAbs that were described recently [28]. Similar to the gp120-sCD4 full-length single chain (FLSC) fusion protein that was shown to be a promising HV-1 vaccine candidate [26, 27], this new type of fusion protein of gp120 with ScFV of bnAb enhancing mAbs, for example, gp120-b12-ScFV and gp120-VRC01-ScFV, can substantially expose the epitopes of all three subgroups of cluster A ADCC mAbs [28], A32 like Abs (N5-i5), C11 like Abs (N12-i3) and Abs competing with both the A32 and C11 (JR4) (FIG. 6). The gp120-VRC01-ScFv also enhances the exposure of epitopes of traditional co-receptor binding CD4i mAbs (N12-i2), similar to the FLSC [26, 27]. The gp120-b12-ScFv stands unique in this

TABLE 4

Profile of epitopes exposure of gp120-ScFv proteins (different from FLSC)
Fold of Ab needed for ELISA binding OD equal to half max on gp120

| Antigen | V1V2/V3 related bnAb | | | CD4bs bnAb | | | CD4i Ab | Cluster A ADCC Ab | | | | | V3 Ab | |
|---|---|---|---|---|---|---|---|---|---|---|---|---|---|---|
| | N60-B1.1 | PG9 | PGT128 | b12 | VRC01 | PG04 | N12-i2 | A32 | N5-i5 | JR4 | C11 | N12-i3 | Glycan 2G12 | N12-O3.1 |
| Bal-gp120 | 1 | 1 | 1 | 1 | 1 | 1 | 1 | 1 | 1 | 1 | 1 | 1 | 1 | 1 |
| FLSC R/T | 16.45[b] | 8.02[b] | 5.07[b] | 46.27[b] | 17.04[b] | >100[b] | 0.01[a] | 0.04[a] | 0.02[a] | 0.11[a] | 0.37[a] | 0.35[a] | 0.91 | 1 |
| gp120-b12-ScFV | 0.01[a] | 0.06[a] | 0.09[a] | >100[b] | 51.44[b] | >100[b] | 36.92[b] | 0.06[a] | 0.02[a] | 0.09[a] | 0.36[a] | 0.23[a] | 0.56 | 1 |
| gp120-VRC01-ScFv | 0.03[a] | 0.09[a] | 0.23[a] | >100[b] | 36.02[b] | >100[b] | 0.01[a] | 0.20[a] | 0.11[a] | 0.32[a] | 0.32[a] | 0.36[a] | 0.66 | 1 |
| gp120-JR4-ScFv | 0.04[a] | 0.02[a] | 0.13[a] | 0.47[a] | 0.44[a] | 0.26[a] | 0.01[a] | >100[b] | >100[b] | >100[b] | >100[b] | >100[b] | 0.61 | 1 |
| gp120-JR48.1-ScFv | 0.14[a] | 0.07[a] | 0.14[a] | 0.56 | 0.53 | 0.36[a] | 0.07[a] | 0.10[a] | 0.08[a] | 0.21[a] | 17.17[b] | 86.81[b] | 0.58 | 1 |

Scale:
Enhancing[a]
Inhibiting[b]

feature that it blocks the exposure of epitopes of traditional co-receptor binding CD4i mAbs (N12-i2).

These Env-ScFV proteins (for example: gp120-b12-ScFV and gp120-VRC01-ScFV) substantially expose the epitopes of bnAbs like N60-B1.1, PG9 and PGT128, as well as epitopes of potent ADCC mAbs like C11-like Ab N5-i5, A32-like AbN12-i3 and N26-i1-like Ab 3.5B. These attractive features of these fusion proteins, therefore, mark them as promising Env vaccine candidates. Immunization with these fusion proteins (individual, combination and sequential) will potentially induce bnAb responses and cluster A ADCC Ab responses against HIV-1.

Bi-specific and Triple-specific Abs Against HIV-1

The findings presented herein that CD4bs bnAbs (b12, VRC01, etc.) as well as cluster A ADCC mAbs (JR4, JR48.1, etc) can enhance the binding of glycan-dependent V1V2 and V3 related bnAbs (N60-B1.1, PG9, PGT128, etc.) to Env also indicate that these three types of non-overlap protective mAbs can be engineered to make bi-specific and triple-specific recombinant human antibodies (FIG. 7). The activity of bi-specific and tri-specific anti-HIV-1 antibodies can be optimized by optimal linker (length) between ScFV and the VH/VL of IgG1 that can result in simultaneous binding of two/three binding domains of the antibodies to the same Env protein. For example, a b12-N60-B1.1 bi-specific Ab (or VRC01-N60-B1.1, JR4-N60-B1.1, b12-PG9, VRC01-PG9, JR4-PG9, etc.) will be much more potent and broad in neutralizing HIV-1 than mixture of individual Abs of b12 and N60-B1.1 (or mixture of VRC01/N60-B1.1, JR4/N60-B1.1, b12/PG9, VRC01/PG9, JR4/PG9, etc. respectively). A JR4-b12-N60-B1.1 triple-specific Ab (or JR4-VRC01-N60-B1.1, JR4-b12-PG9, JR4-VRC01-PG9, etc.) will be much more potent and broad in neutralizing HIV-1 than mixture of individual Abs of JR4, b12 and N60-B1.1 (or mixture of JR4/VRC01/N60-B1.1, JR4/b12/PG9, JR4/VRC01/PG9, etc. respectively).

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Shibata, R., et al., *Neutralizing antibody directed against the HIV-1 envelope glycoprotein can completely block HIV-1/SIV chimeric virus infections of macaque monkeys*. Nature medicine, 1999. 5(2): p. 204-10.
2. Mascola, J. R., et al., *Protection of Macaques against pathogenic simian/human immunodeficiency virus 89.6PD by passive transfer of neutralizing antibodies*. Journal of virology, 1999. 73(5): p. 4009-18.
3. Hessell, A. J., et al., *Effective, low-titer antibody protection against low-dose repeated mucosal SHIV challenge in macaques*. Nature medicine, 2009. 15(8): p. 951-4.
4. Koff, W. C., *HIV vaccine development: Challenges and opportunities towards solving the HIV vaccine-neutralizing antibody problem*. Vaccine, 2011.
5. Walker, L. M., et al., *Broad and potent neutralizing antibodies from an African donor reveal a new HIV-1 vaccine target*. Science, 2009. 326(5950): p. 285-9.
6. Corti, D., et al., *Analysis of memory B cell responses and isolation of novel monoclonal antibodies with neutralizing breadth from HIV-1-infected individuals*. PloS one, 2010. 5(1): p. e8805.
7. Wu, X., et al., *Rational design of envelope identifies broadly neutralizing human monoclonal antibodies to HIV-1*. Science, 2010. 329(5993): p. 856-61.
8. Scheid, J. F., et al., *Sequence and structural convergence of broad and potent HIV antibodies that mimic CD4 binding*. Science, 2011. 333(6049): p. 1633-7.
9. Walker, L. M., et al., *Broad neutralization coverage of HIV by multiple highly potent antibodies*. Nature, 2011. 477(7365): p. 466-70.
10. Wu, X., et al., *Focused evolution of HIV-1 neutralizing antibodies revealed by structures and deep sequencing*. Science, 2011. 333(6049): p. 1593-602.
11. Bonsignori, M., et al., *Analysis of a clonal lineage of HIV-1 envelope V2/V3 conformational epitope-specific broadly neutralizing antibodies and their inferred unmutated common ancestors*. Journal of virology, 2011. 85(19): p. 9998-10009.
12. Wardemann, H., et al., *Predominant autoantibody production by early human B cell precursors*. Science, 2003. 301(5638): p. 1374-7.
13. Scheid, J. F., et al., *Broad diversity of neutralizing antibodies isolated from memory B cells in HIV-infected individuals*. Nature, 2009. 458(7238): p. 636-40.
14. Scheid, J. F., et al., *A method for identification of HIV gp140 binding memory B cells in human blood*. Journal of immunological methods, 2009. 343(2): p. 65-7.
15. Simek, M. D., et al., *Human immunodeficiency virus type 1 elite neutralizers: individuals with broad and potent neutralizing activity identified by using a high-throughput neutralization assay together with an analytical selection algorithm*. Journal of virology, 2009. 83(14): p. 7337-48.
16. Zhou, T., et al., *Structural definition of a conserved neutralization epitope on HIV-1 gp120*. Nature, 2007. 445(7129): p. 732-7.
17. Doores, K. J., et al., *Antibody 2G12 recognizes di-mannose equivalently in domain-and nondomain-exchanged forms but only binds the HIV-1 glycan shield if domain exchanged*. Journal of virology, 2010. 84(20): p. 10690-9.
18. Gorny, M. K., et al., *Identification of a new quaternary neutralizing epitope on human immunodeficiency virus type 1 virus particles*. Journal of virology, 2005. 79(8): p. 5232-7.
19. Krachmarov, C., et al., *Characterization of structural features and diversity of variable-region determinants of related quaternary epitopes recognized by human and rhesus macaque monoclonal antibodies possessing unusually potent neutralizing activities*. Journal of virology, 2011. 85(20): p. 10730-40.
20. Wrammert, J., et al., *Broadly cross-reactive antibodies dominate the human B cell response against 2009 pandemic H1N1 influenza virus infection*. The Journal of experimental medicine, 2011. 208(1): p. 181-93.
21. Sajadi, M. M., et al., *Correlation between circulating HIV-1 RNA and broad HIV-1 neutralizing antibody activity*. Journal of acquired immune deficiency syndromes, 2011. 57(1): p. 9-15.
22. Guan, Y., et al., *Discordant memory B cell and circulating anti-Env antibody responses in HIV-1 infection*. Proceedings of the National Academy of Sciences of the United States of America, 2009. 106(10): p. 3952-7.
23. Kong, L., et al., *Supersite of immune vulnerability on the glycosylated face of HIV-1 envelope glycoprotein gp120*. Nature structural & molecular biology, 2013.
24. Haynes, B. F., et al., *B-cell-lineage immunogen design in vaccine development with HIV-1 as a case study*. Nature biotechnology, 2012. 30(5): p. 423-33.

25. Mouquet, H. and M. C. Nussenzweig, *Polyreactive antibodies in adaptive immune responses to viruses*. Cellular and molecular life sciences: CMLS, 2012. 69(9): p. 1435-45.
26. DeVico, A., et al., *Antibodies to CD4-induced sites in HIV gp120 correlate with the control of SHIV challenge in macaques vaccinated with subunit immunogens*. Proceedings of the National Academy of Sciences of the United States of America, 2007. 104(44): p. 17477-82.
27. Fouts, T. R., et al., *Expression and characterization of a single-chain polypeptide analogue of the human immunodeficiency virus type 1 gp120-CD4 receptor complex*. Journal of virology, 2000. 74(24): p. 11427-36.
28. Guan, Y., et al., *Diverse specificity and effector function among human antibodies to HIV-1 envelope glycoprotein epitopes exposed by CD4 binding*. Proceedings of the National Academy of Sciences of the United States of America, 2013. 110(1): p. E69-78.

What is claimed is:

1. A polypeptide comprising the amino acid sequence set forth in SEQ ID NO:8, termed gp120-b12-ScFV.

2. An immunogenic formulation comprising the polypeptide of claim 1 and a pharmaceutically acceptable carrier and/or adjuvant.

3. A method of generating an immune response in a subject comprising administering an immunologically effective amount of an immunogenic formulation of claim 2 to a subject, thereby generating an immune response in a subject.

* * * * *